(12) United States Patent
Mousa

(10) Patent No.: US 9,580,395 B2
(45) Date of Patent: Feb. 28, 2017

(54) COMPOSITIONS OF DUAL THYROINTEGRIN ANTAGONISTS AND USE IN VASCULAR-ASSOCIATED DISORDERS

(71) Applicant: Vascular Vision Pharmaceutical Company, Rensselaer, NY (US)

(72) Inventor: Shaker A. Mousa, Wynantskill, NY (US)

(73) Assignee: VASCULAR VISION PHARMACEUTICAL COMPANY, Rensselaer, NY (US)

( * ) Notice: Subject to any disclaimer, the term of this patent is extended or adjusted under 35 U.S.C. 154(b) by 76 days.

(21) Appl. No.: 14/510,506

(22) Filed: Oct. 9, 2014

(65) Prior Publication Data

US 2015/0031688 A1 Jan. 29, 2015

Related U.S. Application Data

(62) Division of application No. 12/916,714, filed on Nov. 1, 2010, now Pat. No. 8,859,539.

(60) Provisional application No. 61/280,235, filed on Nov. 2, 2009.

(51) Int. Cl.
| | |
|---|---|
| C07D 279/12 | (2006.01) |
| A61K 31/195 | (2006.01) |
| A61K 31/24 | (2006.01) |
| A61K 31/27 | (2006.01) |
| C07C 271/22 | (2006.01) |
| A61K 31/4406 | (2006.01) |
| A61K 31/54 | (2006.01) |
| C07C 217/20 | (2006.01) |
| C07C 239/12 | (2006.01) |
| C07C 271/16 | (2006.01) |
| C07C 275/24 | (2006.01) |
| C07C 279/08 | (2006.01) |
| C07D 213/36 | (2006.01) |
| C07D 295/155 | (2006.01) |
| C07D 213/55 | (2006.01) |

(52) U.S. Cl.
CPC .......... *C07D 279/12* (2013.01); *A61K 31/195* (2013.01); *A61K 31/24* (2013.01); *A61K 31/27* (2013.01); *A61K 31/4406* (2013.01); *A61K 31/54* (2013.01); *C07C 217/20* (2013.01); *C07C 239/12* (2013.01); *C07C 271/16* (2013.01); *C07C 271/22* (2013.01); *C07C 275/24* (2013.01); *C07C 279/08* (2013.01); *C07D 213/36* (2013.01); *C07D 213/55* (2013.01); *C07D 295/155* (2013.01)

(58) Field of Classification Search
CPC .............................. C07C 239/12; A61K 31/195
See application file for complete search history.

(56) References Cited

PUBLICATIONS

Avery et al, Ophthalmology, Intravitreal Bevacizumab (Avastatin) in the Treatment of Proliferative Diabetic Retinopathy, 2006, 113, pp. 1695-1705.*
Yokoyama et al, Journal of Medicinal Chemistry, Synthesis and Structure-Activity Relationships of Oxamic Acid and Acetic Acid Derivatives Related to L-Thyronine1995, 38, pp. 695-707. Annotated.*
Rebbaa et al., Novel Function of the thyroid hormone analog tetraiodothyroacetic acid: a cancer chemosensitizing and anti-cancer agent, Angiogenesis (2008) 11:269-276 DOI 10.1007/s10456-008-9110-8.
Mousa et al., Proangiogenesis Action of the Thyroid Hormone Analog 3,5-Diiodothyropropionic Acid (DITPA) Is Initiated at the Cell Surface and Is Integrin Mediated, Endocrinology 147(4):1602-1607, Copyright 2006 by the Endocrine Society doi: 10.1210/en.2005-1390.
Shaker A. Mousa, Anti-integrins as a potential therapeutic target in angiogenesis, 1999 Copyright Ashley Publications Ltd. ISSN 1354-3776, pp. 1237-1248.
Shaker A. Mousa, αv Vitronectin Receptors in Vascular-Mediated Disorders, Medicinal Research Reviews, vol. 23, No. 2, 190-199, 2003, Copyright 2002 Wiley Periodicals, Inc.
Kerr et al, THE αv integrin antagonists as novel anticancer agents: an update, 2002 copyright Ashley Publications Ltd ISSN 1354-3784, pp. 1765-1774.
Henry et al., Vitronectin Receptor—αv B3 Integrin—Antagonists: Chemical and Structural Requirements for Activity and Selectivity, 1389-5575/02, copyright 2002 Bentham Science Publishers, Ltd., Mini Reviews in Medicinal Chemistry, 2002, 531-542.
Yokoyama et al., Synthesis and Structure-Activity Relationships of Oxamic Acid and Acetic Acid Derivatives Related to L-Thyronine, 0022-2623/95/1838-0695 copyright 1995 American Chemical Society, J. Med. Chem. 1995, 38, 695-707.
Wang et al., First Enantioselective Total Synthesis of (-)-Tejedine, Orangic Letters, 2002, vol. 4, No. 16, pp. 2675-2678.
Lv et al., Copper-Catalyzed Direct Aryl Quaternization of N-subsituted Imidazoles to Form Imidazolium Salts, JOC, The Journal of Organic Chemistry, dx.doi.org/10.1021/jo400527rl J. Org. Chem. 2013, 78, pp. 5723-5730.
Everson et al., Nickel-Catalyzed Reductive Cross-Coupling of Aryl Halides with Alkyl Halides, JACS Communications, 920 J. Am. Chem. Soc. 2010, 132, pp. 920-921, 10.1021/ja9093956, 2010 American Chemical Society.
Wang et al., N-Substituted homopiperazine barbiturates as gelatinase inhibitors, Bioorganic & Medicinal Chemistry, 0968-0896/$—see front matter copyright 2011 Elsevier Ltd. All rights reserved, doi:10.1016/j.bmc.2011.06.055, Bioorg. Med. Chem. 19 (2011) pp. 4985-4999.
Hosoya et al., Total Synthesis of the Gilvocarcins, 0002-7863/94/1516-1004$04.50/0, copyright 1994 American Chemical Society, J. Am. Chem. Soc. 1994, 116, 1004-1015.
Seoane, Acidic Rearrangement of (Benzyloxy) chalcones: A Short Synthesis of Chamanetin, Synthesis 2009, No. 24, pp. 4190-4202, Advanced online publication: Oct. 22, 2009, DOI: 10.1055/s-0029-1217064; Art ID: M03209SS copyright Georg Thieme Verlag Stuttgart—New York.

(Continued)

*Primary Examiner* — Paul A Zucker
(74) *Attorney, Agent, or Firm* — Schmeiser, Olsen & Watts, LLP

(57) ABSTRACT

A dual thyrointegrin antagonist and a method for treating an angiogenesis-mediated disorder and/or a hyperthyroidism disorders by introducing the dual thyrointegrin antagonist into animals (e.g., mammals, human beings). The dual thyrointegrin antagonist includes a chemical structure having a thyroid hormone antagonist and αvβ3 integrin antagonist in the same molecule.

5 Claims, 16 Drawing Sheets

(56) References Cited

PUBLICATIONS

De Luca, L; Porcheddu, A; Giacomelli, G; Murgia, I. Microwave-assisted synthesis of N-monosubstututed urea derivatives. Synlett. 2010, 2439-2442.

Knight, DW; Leese, MP. A survey of suitable protecting groups for the synthesis of hydroxylamines by Mitsunobu reactions. Tet. Lett. 2001, 42, 2593-2595.

Walwil, AM. Synthesis of N-[5-(guanidinopentyl)]-N[3-[(3-methyl-1-oxo-2-butenyl)]-amino]-propyldodecamide. Res. J. Chem. Environ. 2006, 12, 70-75.

Examiner's Amendment (Aug. 8, 2014) for U.S. Appl. No. 12/916,714, filed Nov. 1, 2010.

Notice of Allowance (Jun. 12, 2014) for U.S. Appl. No. 12/916,714, filed Nov. 1, 2010.

Final amendment (May 29, 2014) for U.S. Appl. No. 12/916,714, filed Nov. 1, 2010.

Final Office Action (Apr. 1, 2014) for U.S. Appl. No. 12/916,714, filed Nov. 1, 2010.

Amendment (Jan. 15, 2014) for U.S. Appl. No. 12/916,714, filed Nov. 1, 2010.

Office Action (Sep. 18, 2013) for U.S. Appl. No. 12/916,714, filed Nov. 1, 2010.

Amendment (Sep. 3, 2013) for U.S. Appl. No. 12/916,714, filed Nov. 1, 2010.

Office Action (Mar. 4, 2013) for U.S. Appl. No. 12/916,714, filed Nov. 1, 2010.

Response to Restriction (Jan. 28, 2013) for U.S. Appl. No. 12/916,714, filed Nov. 1, 2010.

Restriction (Dec. 27, 2012) for U.S. Appl. No. 12/916,714, filed Nov. 1, 2010.

* cited by examiner

COMPOSITIONS OF DUAL THYROINTEGRIN ANTAGONISTS AND USE IN VASCULAR-ASSOCIATED DISORDERS

CROSS-REFERENCES TO RELATED APPLICATIONS

This application is a divisional application claiming priority to U.S. patent application Ser. No. 12/916,714, filed Nov. 1, 2010, now U.S. Pat. No. 8,859,539, issued Oct. 14, 2014, which claimed priority to a Provisional No. 61/280,235, filed on Nov. 2, 2009, which is incorporated herein by reference in its entirety.

FIELD OF THE INVENTION

The present invention provides a dual thyrointegrin antagonist and a method for using the dual thyrointegrin antagonist to treat an angiogenesis-mediated disorder and/or a hyperthyroidism disorders

BACKGROUND OF THE INVENTION

The thyroid hormone antagonist such as tetrac (compound 8, FIG. 1) has been shown to inhibit angiogenesis through weak affinity binding to cell surface receptor $\alpha v \beta_3$ [Rebbaa A, Chu F, Davis F B, Davis P J, Mousa S A, Novel function of the thyroid hormone analog tetraiodothyroacetic acid: a cancer chemosensitizing and anti-cancer agent, Angiogenesis, 2008, 11: 269-76]. However, tetrac translocates into the cell nucleus interfering with thyroid hormone nuclear function leading to undesirable side effects.

Thus there is a need for a thyroid hormone antagonist that does not interfere with thyroid hormone nuclear function.

SUMMARY OF THE INVENTION

The present invention provides a dual thyrointegrin antagonist, comprising a chemical structure of

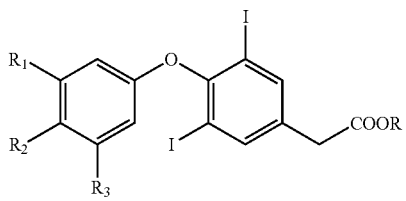

wherein R is selected from the group consisting of hydrogen, methyl, ethyl, propyl, and isopropyl;

wherein a group X is —$(CH_2)_n NH_2$ such that n is 3, 4, or 5;

wherein a first condition, a second condition, a third condition, a fourth condition, or a fifth condition is satisfied;

wherein the first condition is that ($R_1$ is X, $R_2$ is I, and $R_3$ is I), ($R_1$ is I, $R_2$ is X, and $R_3$ is I), or ($R_1$ is I, $R_2$ is I, and $R_3$ is X);

wherein the second condition is that $R_1$, $R_2$, and $R_3$ are each selected from the group consisting of X, H, and I such that $R_1$, $R_2$, and $R_3$ differ from each other;

wherein the third condition is that $R_1$, $R_2$, and $R_3$ are each selected from the group consisting of X, OH, and I such that $R_1$, $R_2$, and $R_3$ differ from each other;

wherein the fourth condition is that $R_1$, $R_2$, and $R_3$ are each selected from the group consisting of X, OH, and H such that $R_1$, $R_2$, and $R_3$ differ from each other; and wherein the fifth condition is that $R_1$ is I, $R_3$, is I, and $R_2$ is selected from the group consisting of

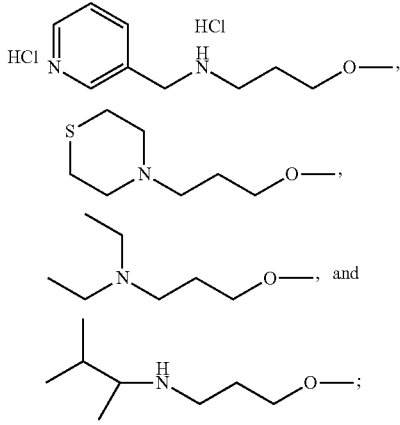

and wherein t-Boc stands for tert-Butyloxycarbonyl.

The present invention provides a dual thyrointegrin antagonist, comprising a chemical structure of

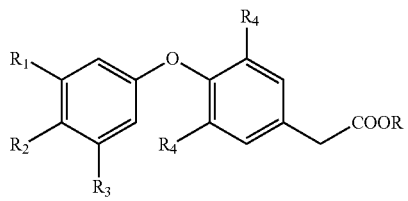

wherein R is selected from the group consisting of hydrogen, methyl, ethyl, propyl, and isopropyl;

wherein a group Y is selected from the group consisting of

OH,

—$(CH_2)_n NH_2$ such that n is 3, 4, or 5,

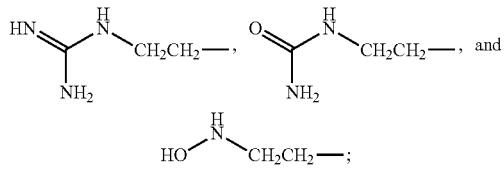

wherein a group $R_5$ is

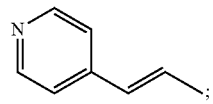

wherein a group $R_6$ is

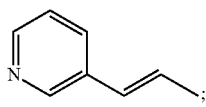

wherein a group $R_7$ is

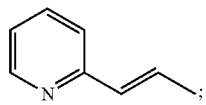

wherein a group $R_8$ is

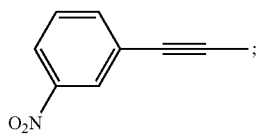

wherein a group $R_9$ is

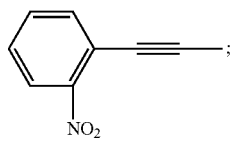

wherein a group $R_{10}$ is selected from the group consisting of $R_5$, $R_6$, and $R_7$;
wherein a group $R_{11}$ is selected from the group consisting of $R_8$ and $R_9$;
wherein a first condition, a second condition, a third condition, a fourth condition, or a fifth condition is satisfied;
wherein the first condition is that ($R_1$ is I, $R_2$ is Y, $R_3$ is I, and $R_4$ is I), ($R_1$ is Y, $R_2$ is I, $R_3$ is I, and $R_4$ is I), or ($R_1$ is I, $R_2$ is I, $R_3$ is Y, and $R_4$ is I);
wherein the second condition is that ($R_1$ is i-Pr, $R_2$ is Y, $R_3$ is i-Pr, and $R_4$ is Br), ($R_1$ is Y, $R_2$ is i-Pr, $R_3$ is i-Pr, and $R_4$ is Br), or ($R_1$ is i-Pr, $R_2$ is i-Pr, $R_3$ is Y, and $R_4$ is Br);
wherein the third condition is that $R_4$ is Br and that $R_1$, $R_2$, and $R_3$ are each selected from the group consisting of Y, i-Pr, and $R_{10}$ such that $R_1$, $R_2$, and $R_3$ differ from each other;
wherein the fourth condition is that $R_4$ is methyl and that $R_1$, $R_2$, and $R_3$ are each selected from the group consisting of Y, i-Pr, and $R_{11}$ such that $R_1$, $R_2$, and $R_3$ differ from each other;
wherein the fifth condition is that $R_4$ is t-butyl and that $R_1$, $R_2$, and $R_3$ are each selected from the group consisting of Y, i-Pr, and H such that $R_1$, $R_2$, and $R_3$ differ from each other;
wherein i-PR stands for isopropyl.

The present invention advantageously provides a dual thyrointegrin antagonist that does not interfere with thyroid hormone nuclear function.

BRIEF DESCRIPTION OF THE DRAWINGS

The file of this patent contains at least one drawing executed in color. Copies of this patent with color drawing(s) will be provided by the Patent and Trademark Office upon request and payment of the necessary fees.

DETAILED DESCRIPTION OF THE INVENTION

Synthetic $\alpha v \beta_3$ antagonist is a potent inhibitor of angiogenesis by binding to the cell surface receptor alphavbeta3 ($\alpha v \beta_3$) integrin [Mousa S A, O'Connor L, Davis F B, Davis P J, Pro-angiogenesis action of the thyroid hormone analog 3,5-diiodothyropropionic acid (DITPA) is initiated at the cell surface and is integrin mediated, Endocrinology, 2006, 147: 1602-7; Mousa S A, Anti-integrins as a potential therapeutic target in angiogenesis, Expert Opin Ther Pat. 1999, 9: 1237-48].

The present invention provides a chemical structure serving as dual Thyrointegrin antagonist, namely a thyroid hormone antagonist (e.g., tetrac) and an $\alpha v \beta_3$ antagonist in the same molecule to enhance cell surface receptor binding, which is a new strategy in which the stereo chemical and biological properties are combined to design novel dual thyroid and integrin (Thyrointegrin) antagonists.

A new dual antagonist drug of the present invention provides a compound having a chemical structure that provides an association of a Thyroid Receptors (TR) antagonist (e.g., tetrac) and the common pharmacophoric groups to alphav/beta3 antagonists.

Figure 1:
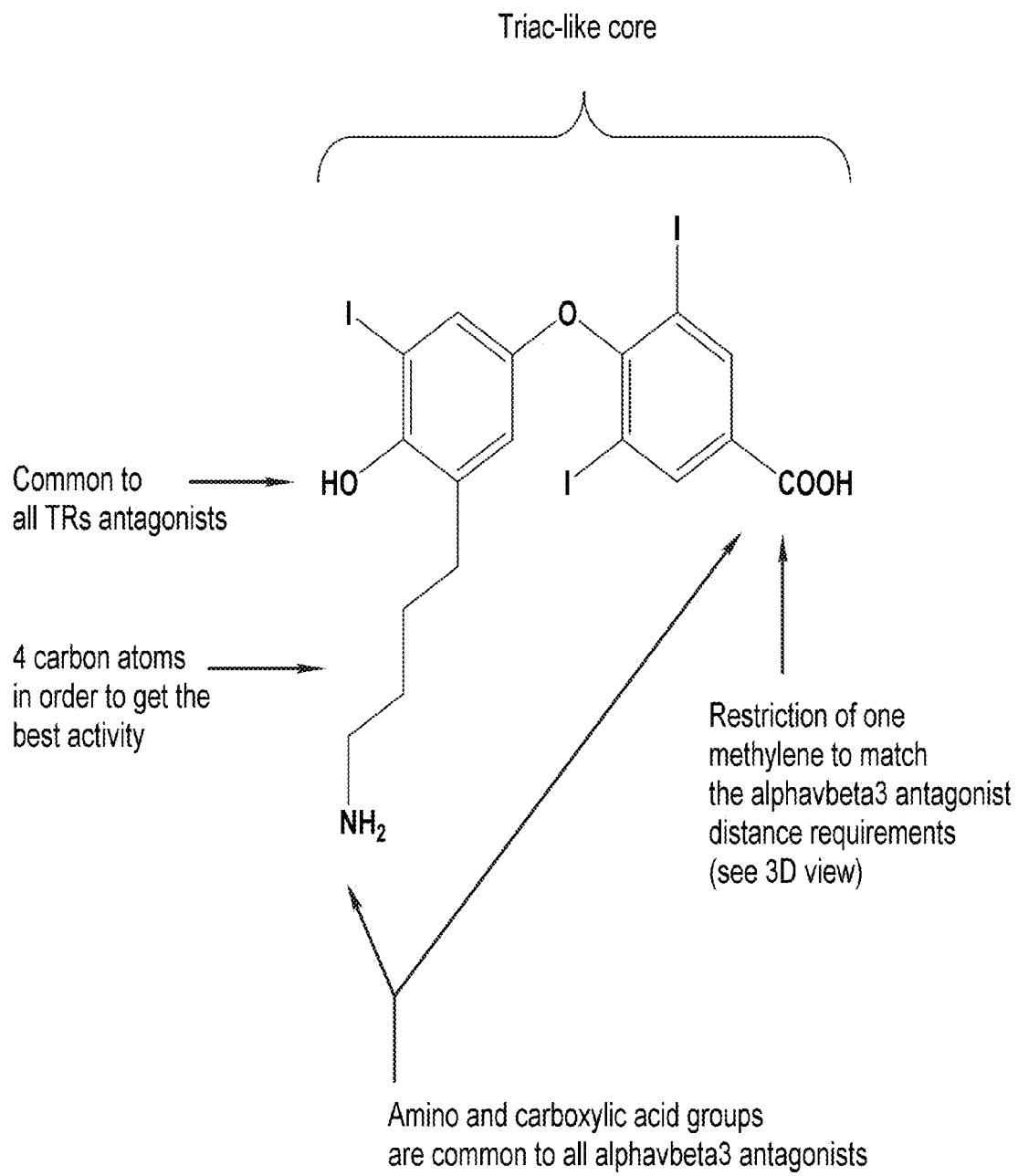
FIG. 1 depicts a novel compound of the present invention having carboxylic acid (COOH) and amino (NH2) ends, along with indicated characteristics of the novel compound.

FIG. 1 depicts a novel compound of the present invention having carboxylic acid (COOH) and amino (NH2) ends, along with indicated characteristics of the novel compound.

Figure 2:
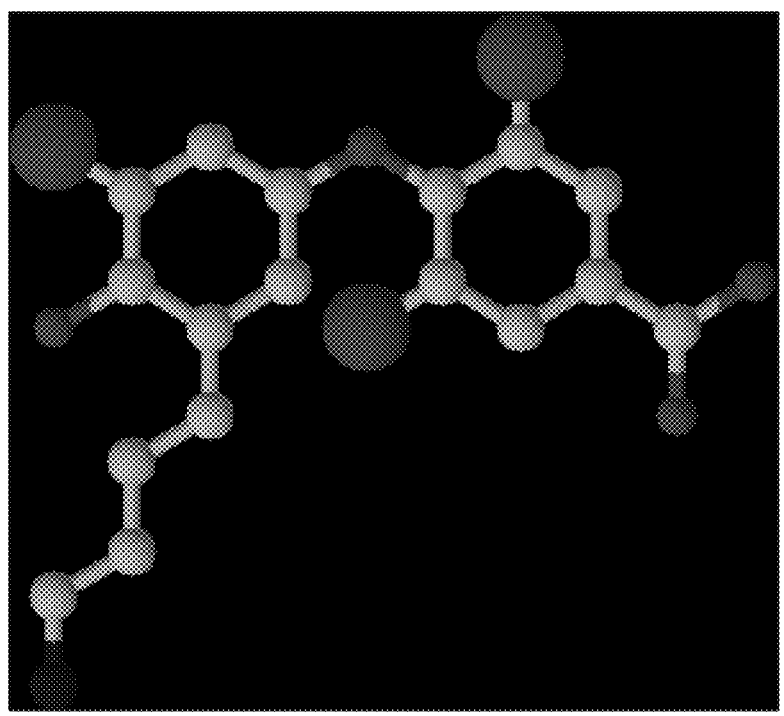
FIG. 2 depicts a three dimensional view of the compound of FIG. 1, in accordance with embodiments of the present invention.

FIG. 2 depicts a three dimensional view of the compound of FIG. 1, in accordance with embodiments of the present invention. This three dimensional view and the atoms distance were realized and calculated using ACD 3D Viewer.

The compound in FIG. 2, when drawn planar, has a distance of 11.8 Å between the amino and carboxylic acid ends. In its natural crystal form, the compound in FIG. 2 might have its aromatic rings positioned perpendicular to each other, which might even more reduce the inner distance between the two functional groups to promote an activity over the alphav-beta3 target.

Representative thyroid antagonists A, B, C, D, E, F, G, and H within the scope of the present invention are as follows:

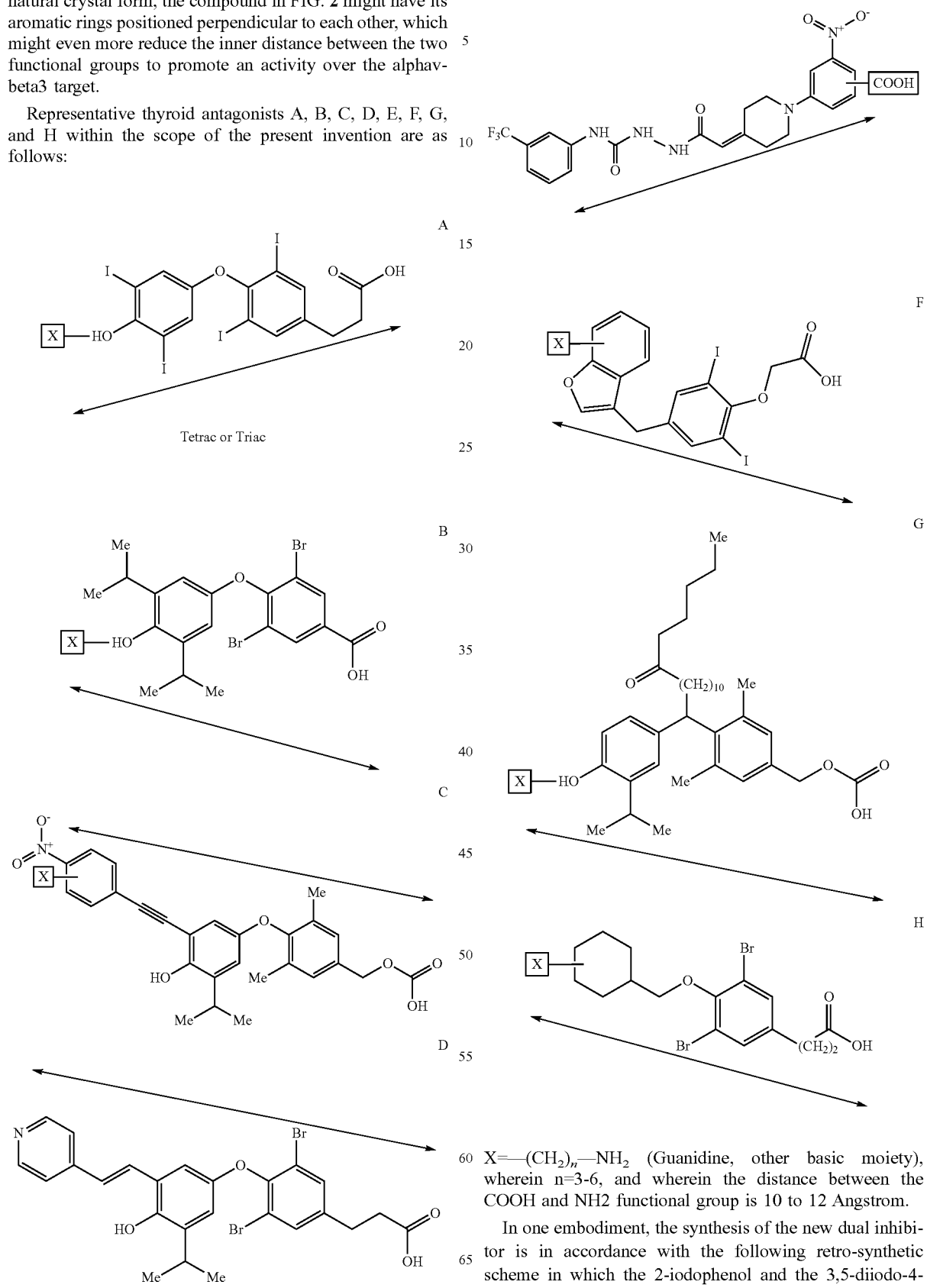

X=—(CH$_2$)$_n$—NH$_2$ (Guanidine, other basic moiety), wherein n=3-6, and wherein the distance between the COOH and NH2 functional group is 10 to 12 Angstrom.

In one embodiment, the synthesis of the new dual inhibitor is in accordance with the following retro-synthetic scheme in which the 2-iodophenol and the 3,5-diiodo-4-hydroxybenzoic acid may both be commercially available:

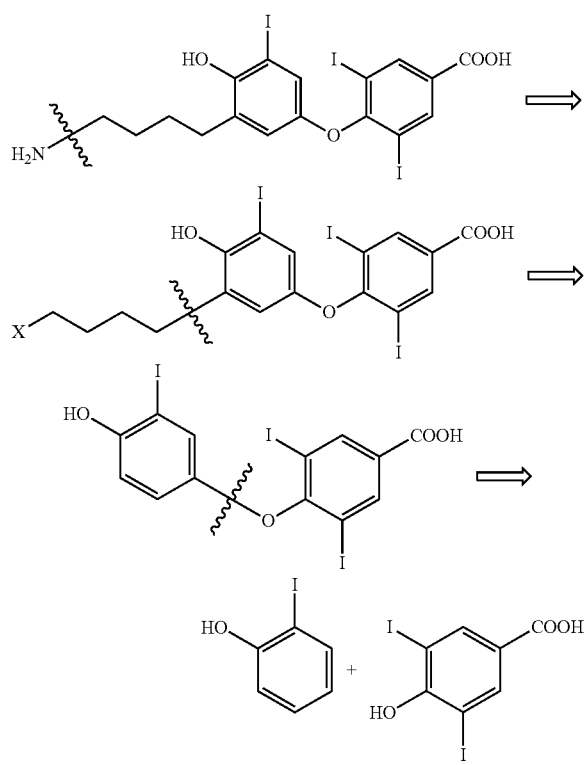

Figure 3:
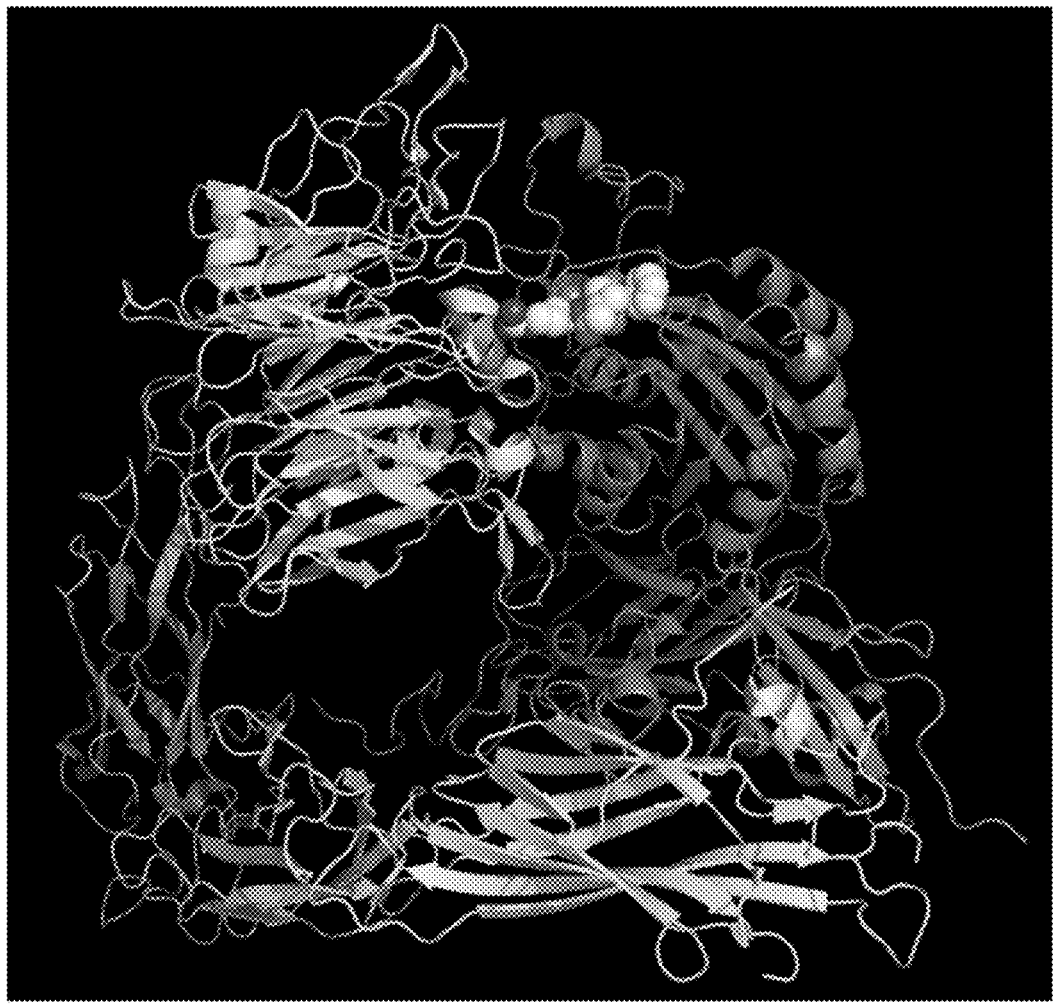
FIG. 3 depicts a crystal structure of αvβ3 integrin RGD cyclic peptide complex, in accordance with embodiments of the present invention.

FIG. 3 depicts a crystal structure of αvβ3 integrin RGD cyclic peptide complex (PDB: 1L5G). In FIG. 3, the αv-sub-unit is in yellow, the β3 A domain is in purple, and the RGD cyclic peptide is in solid white.

Figure 4:
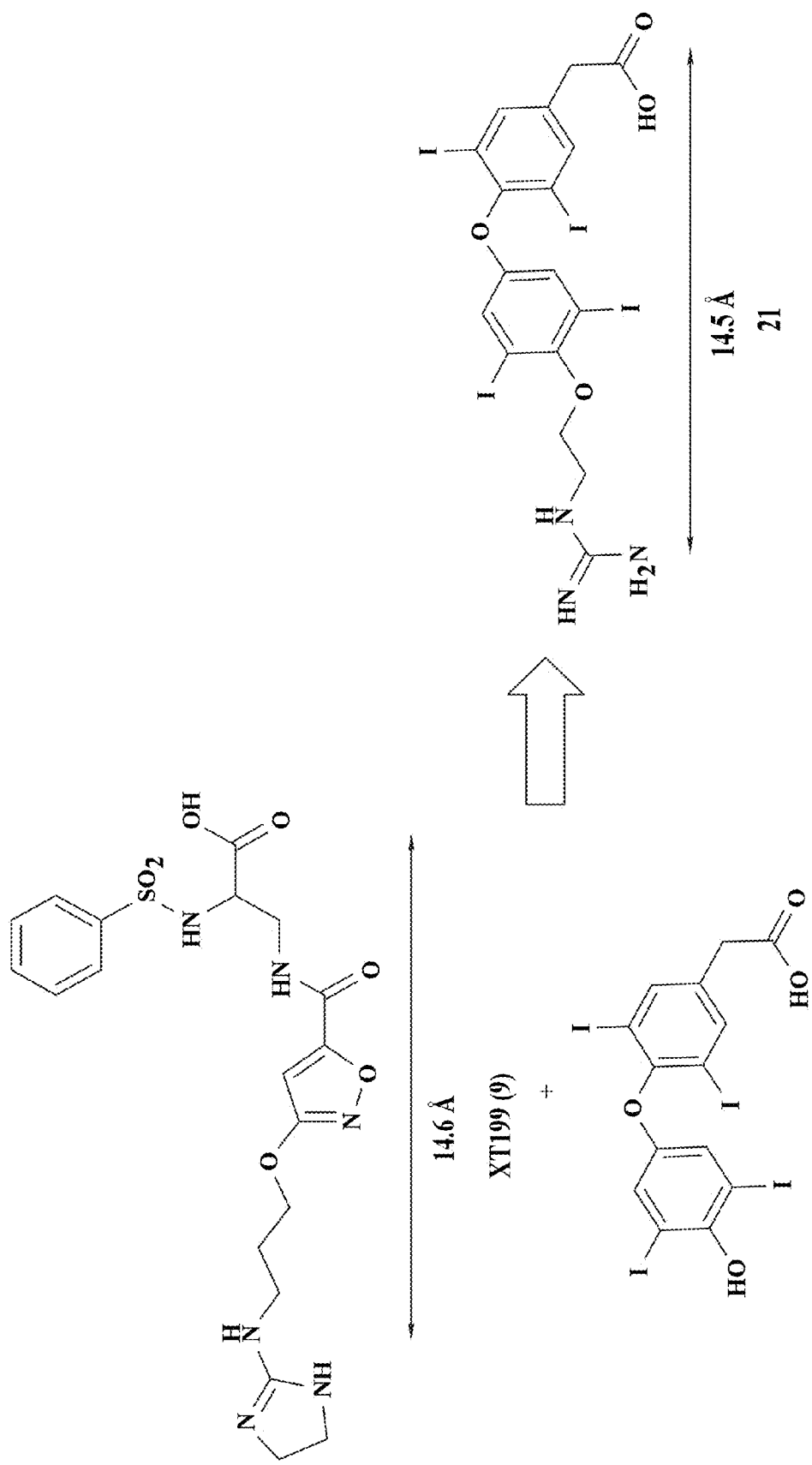
FIG. 4 depicts a schematic of the design of novel dual thyrointegrin antagonists showing inter-point distances, in accordance with embodiments of the present invention.

FIG. 4 depicts a schematic of the design of novel dual Thyrointegrin antagonists showing inter-point distances. In FIG. 4, the stereo-chemical and biological properties of tetrac (8) and XT199 (9) are combined in the resultant compound (21). The novel compound 21 possesses unprecedented anti-angiogenesis activity and the possibility to interact in the nanomolar concentration range with both the thyroid receptor TR1 and the integrin $α_vβ_3$ which are both configured to participate in the angiogenesis process.

Computer-Aided Design of Dual Thyrointegrin Inhibitors

Classical and new molecular modeling approaches using the lock and key model to investigate ligand binding to integrin $α_vβ_3$ was investigated in accordance with the present invention. The most commonly used methods are DOCK and Autodock. These tools can be used to characterize ligand-integrin interactions at the atomic level, as well as define quantitative structure-activity relationships, with somewhat different outcomes. Autodock is programmed to allow torsional flexibility in ligands to optimize binding, whereas DOCK uses a different algorithm to match points located within the binding site and ligand.

In the current study of the present invention, simulated docking of a known ligand to integrin $α_vβ_3$ was performed using FlexX version 3.1.2 (BioSolveIT GmbH) which revealed to be a useful tool to analyze the analogues of tetrac. The active site was defined as all amino acids in their entirety containing any atom within 15 Å of any atom of the cyclic peptide ligand. The ligand was then removed, but the three active site manganese ions were retained, as they participate in ligand binding. The receptor was not further modified, and was treated as rigid during the docking procedure. FlexX uses incremental construction; thus, each compound was first fragmented into components before docking Qualitative interactions for the first fragment were identified, after which the complete compound was constructed by linking the remaining components step-by-step. After the addition of each component, new interactions were defined, and the scoring function was used to select the best partial solution. This was repeated until reconstruction of the original ligand was complete. Of the 30 different solutions generated by FlexX, the best one was chosen based on FlexX score and position within the active site.

For the integrin $α_vβ_3$ to exert its angiogenesis-mediated disorders, intracellular activation, known to induce conformational changes to the active state, would allow physiologic ligands to bind. Structural data reported in the literature characterized the binding of the tripeptide Arg-Gly-Asp sequence of the natural ligands to occur at the interface of the propeller of the $α_vβ_3$ and the βA region. Co-crystallization studies justified that this binding site was the only part of the protein to come under the influence of any ligand.

With the present invention, small conformational changes and coordination of one of the metal ions were induced at the time of the binding. The tripeptide sequence, tetrac and XT199 were docked to observe the ligand-receptor interactions with precision and to understand how to modulate tetrac to enhance its fit in the binding site. Docking of all compounds to integrin $α_vβ_3$ was performed by FlexX version 3.1.2 (BioSolveIT GmbH). The 3D structure of the receptor was taken from the crystal structure of the extra-cellular segment of integrin $α_vβ_3$ in complex with a cyclic peptide ligand, available in the Protein DataBase (1L5G). The active site was defined as all complete amino acids containing any atom within 15 Å of any atom of the cyclic peptide ligand. The ligand was then removed, but the 3 manganese ions were kept in the active site as they were taking part of the binding of the ligand. The receptor was not further modified and treated rigid during the docking procedure. As FlexX use incremental construction, each compound to dock was first fragmented into components. Once the first fragment has found qualitative interactions, the complete compound is constructed by linking the remaining components step by step. After adding one component, new interactions are searched and the scoring function is used to select the best partial solutions, until complete reconstruction of the original ligand. From the 30 different solutions given by FlexX, the best solution was chosen according to its FlexX Score and its pose within the active site.

The cyclic tripeptide occupied the shallow crevice between the propeller and the βA units in the integrin head with the Arg and Asp residues exclusively contacting the propeller and βA domains, respectively (Asp chelated the metal ion at a distance of 2.6 Å). Following this method, the docked tripeptide sequence was consistent with known molecular modelling of the high affinity ligand. Tetrac and XT199 were also modelled with the integrin. Very detailed magnified pictures allowed characterizing all potential interactions of each molecule with the integrin. For each compound docked, the carboxylic acid proved to be responsible for the main ligand receptor interaction by chelating the metal ion (d=2.6 Å from the metal ion), reported to take place on the activated integrin only. In that region, the phenyl sulphonamide ramification of XT199 stabilized the chelation by an interaction with the Arg 214. The interaction of tetrac with the metal ion was stabilized by an electrostatic interaction with the vicinal Asn 215 and a clear H-bond interaction of the OH of the phenol with Tyr 178. XT199 was the only one to interact with the Arg recognition site in the propeller domain of $α_vβ_3$; the imidazole amine found a best fit between Asp 150 and Asp 218. Moreover, the superposition of the structures of the integrin antagonist with the tripeptide clearly showed an exact same spatial orientation.

To shift the antagonist strength of tetrac upwards, its template structure was modified to reach anchorage in the integrin binding site due to an alkyl chain carrying at least an amino group. In order to do so, several nanomolar non peptide integrin antagonists were considered (from works reported by several pharmaceutical companies) in addition to XT199. This led to design novel structures of compounds, some dual thyrointegrin antagonists. Add-ons to the structure of tetrac were selected in priority for the interaction with the Arg recognition site in the propeller domain they could bring. Also it was attempted to satisfy the desired distance between the carboxylic acid and the amino group, which should have been the same distance as the distance between the same groups in XT199. The selected functional groups were an amino pyridine, a guanidine, a urea and an amine.

Molecular modeling and co-crystallization studies have been carried out in accordance with the present invention to refine the binding interactions of natural ligands to integrin $\alpha_v\beta_3$ at the atomic level. These types of analyses have shown that the interface of the propeller of the $\alpha_v\beta_3$ subunit and the βA region (the head of the protein) is the only portion of the receptor that participates in binding to ligand.

Figure 5A:
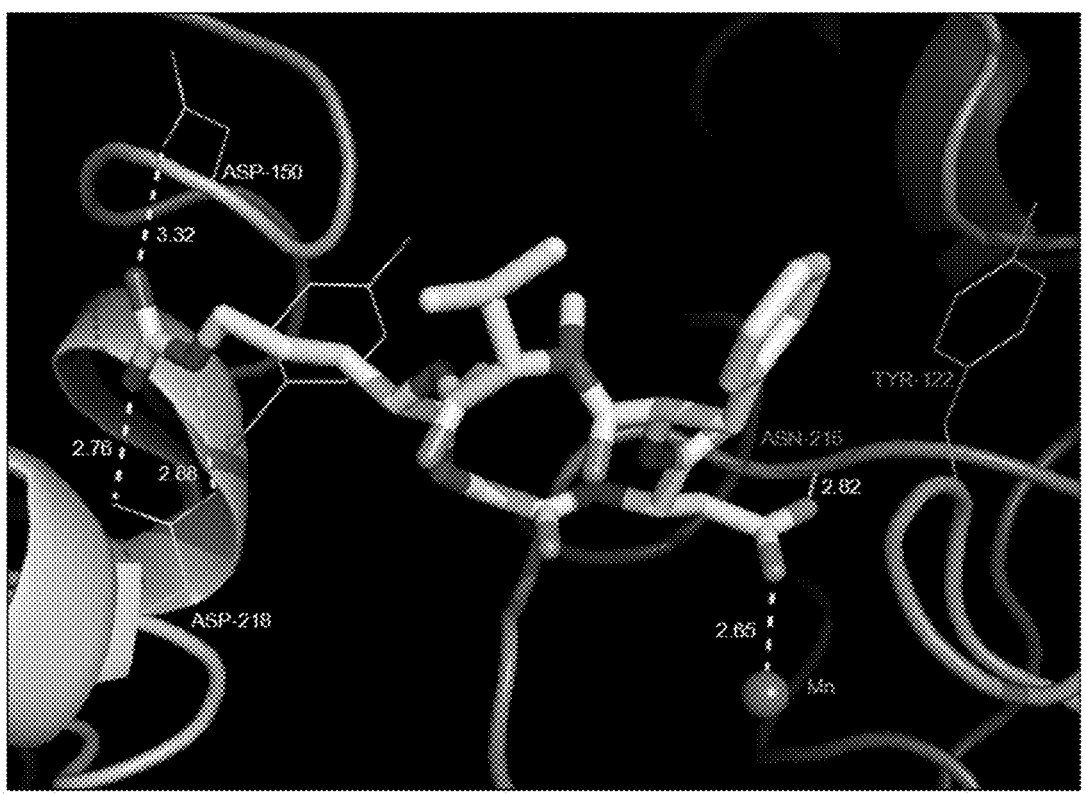
FIG. 5A depicts binding of ligand to αvβ3 integrin, in accordance with embodiments of the present invention.

FIG. 5A depicts binding of ligand to αvβ3 integrin, in accordance with embodiments of the present invention. The blue ball represents the manganese ion and yellow dotted lines illustrate H-bond interactions.

Figure 5B:
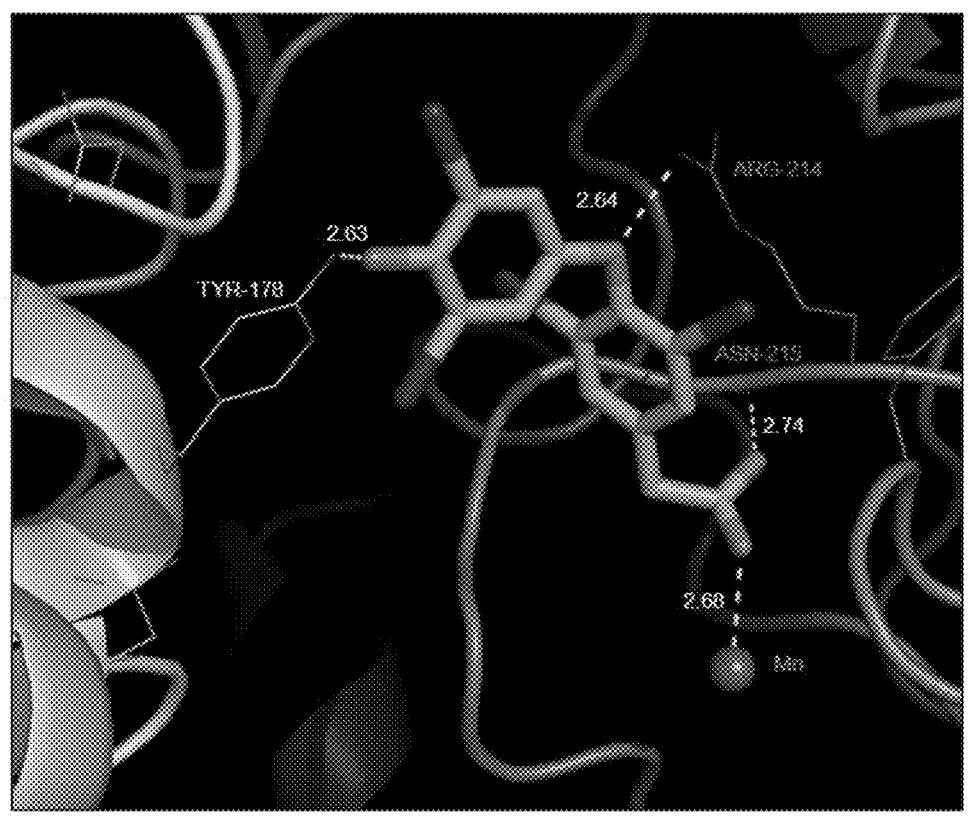
FIG. 5B depicts binding of tetrac to αvβ3 integrin, in accordance with embodiments of the present invention.

FIG. 5B depicts binding of tetrac to αvβ3 integrin, in accordance with embodiments of the present invention. The blue ball represents the manganese ion and yellow dotted lines illustrate H-bond interactions. Tetrac (green) is bound at the interface of the αvβ3 integrin αv-subunit (yellow) and β3A domain (purple).

Figure 5C:
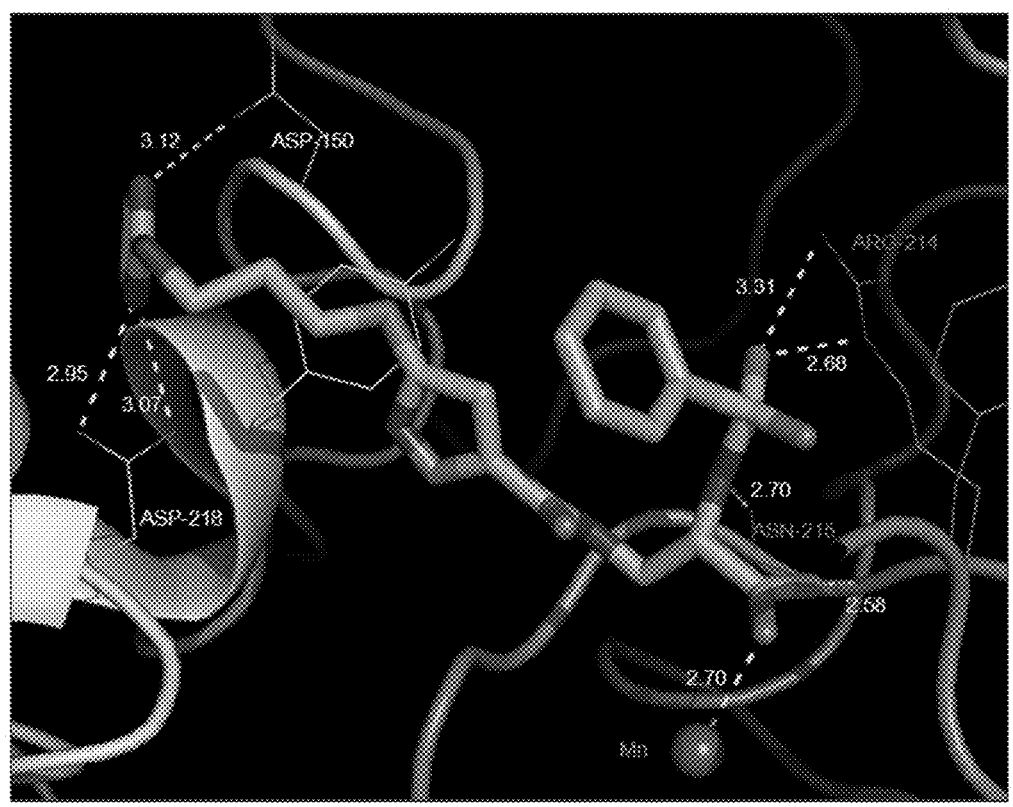
FIG. 5C depicts binding of XT199 to αvβ3 integrin, in accordance with embodiments of the present invention.

FIG. 5C depicts binding of XT199 to αvβ3 integrin, in accordance with embodiments of the present invention. The blue ball represents the manganese ion and yellow dotted lines illustrate H-bond interactions. XT199 (green) is bound at the interface of the αvβ3 integrin αv-subunit (yellow) and β3A domain (purple).

Figure 5D:
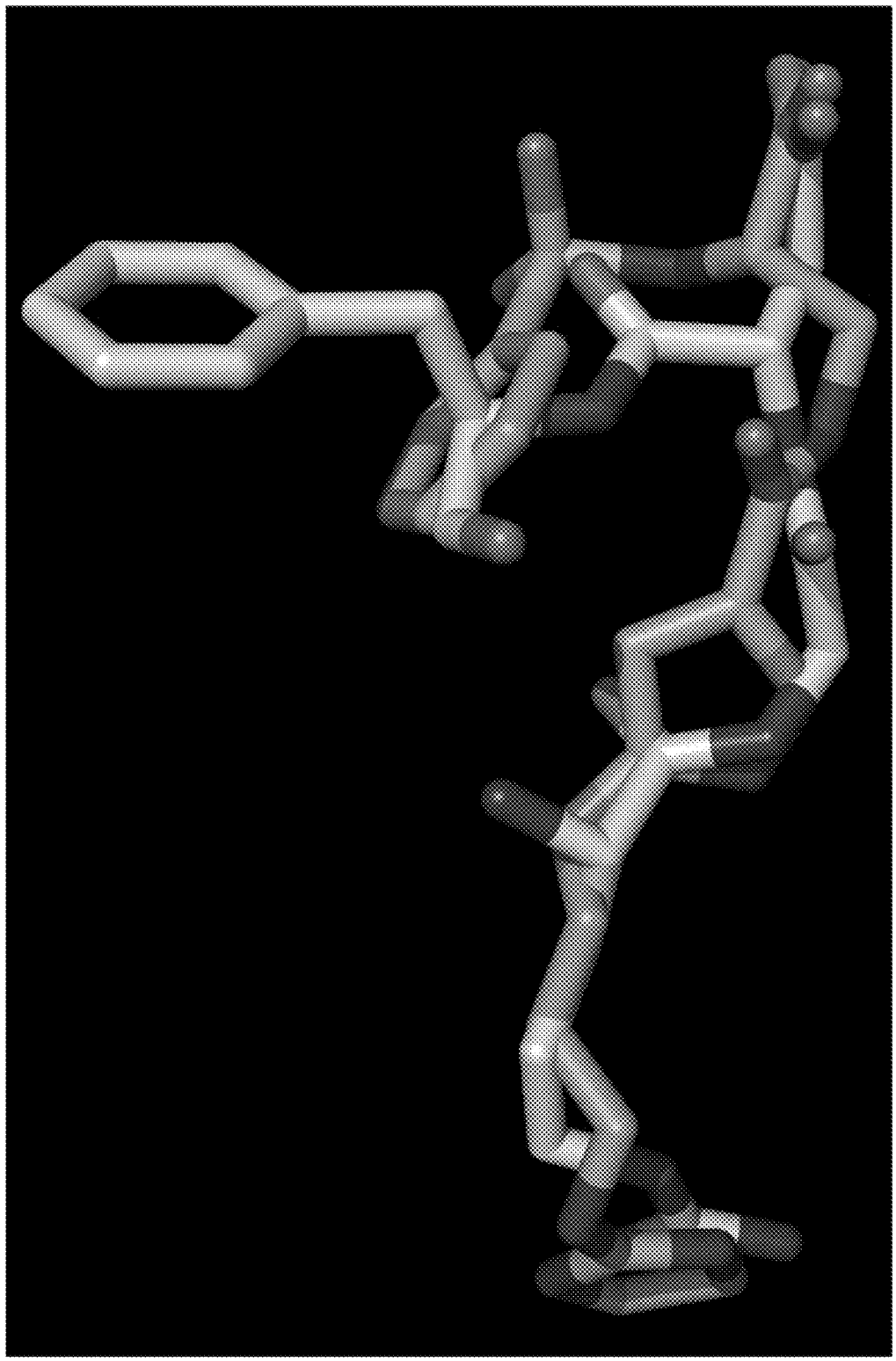
FIG. 5D depicts superimposition of RGDF and XT199, in accordance with embodiments of the present invention.
Figure 6A:
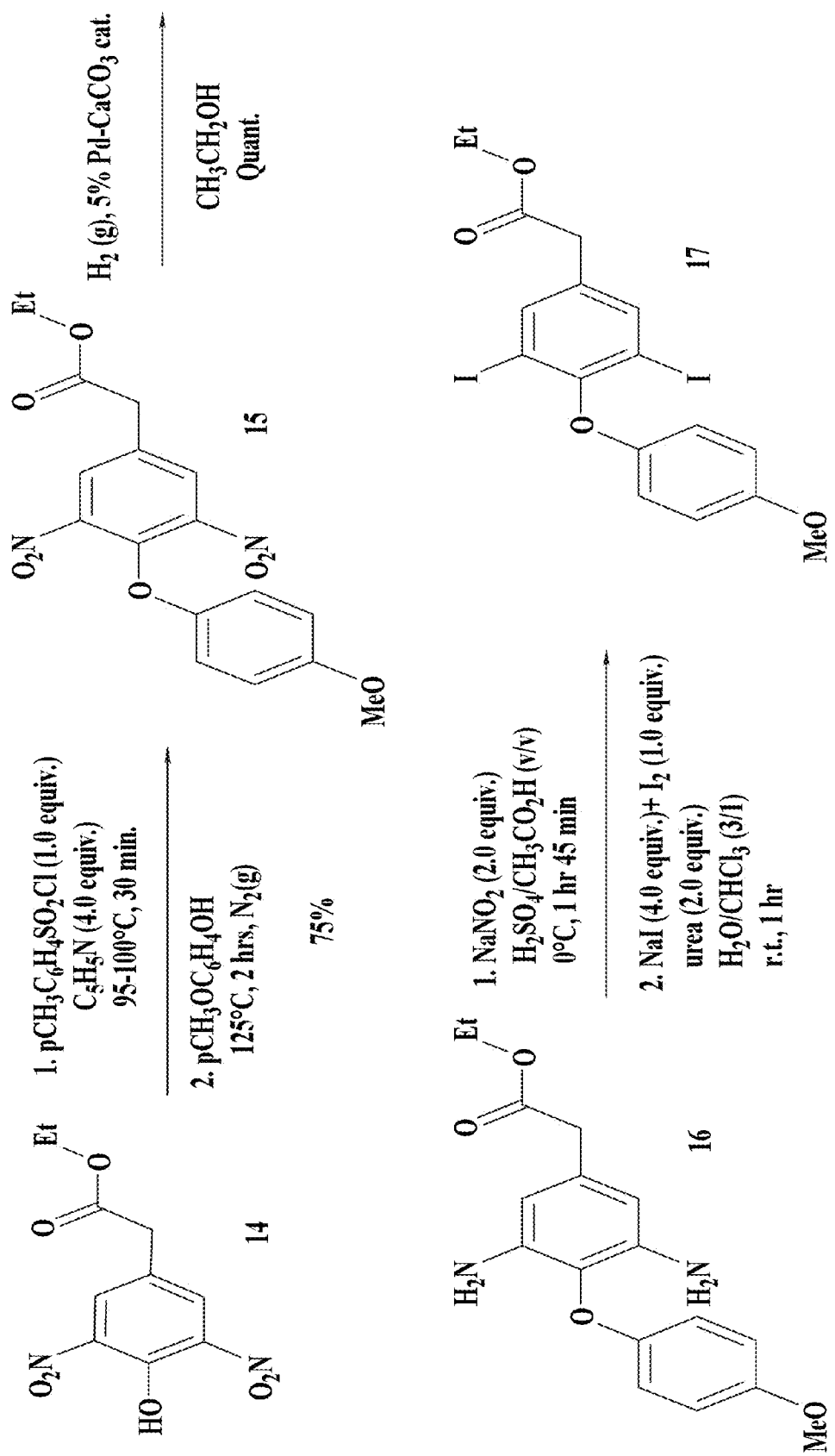
FIGS. 6A, 6B, 6C, and 6D outline a linear synthetic pathway for the preparation of dual Thyrointegrin inhibitors, in accordance with embodiments of the present invention.
Figure 6B:
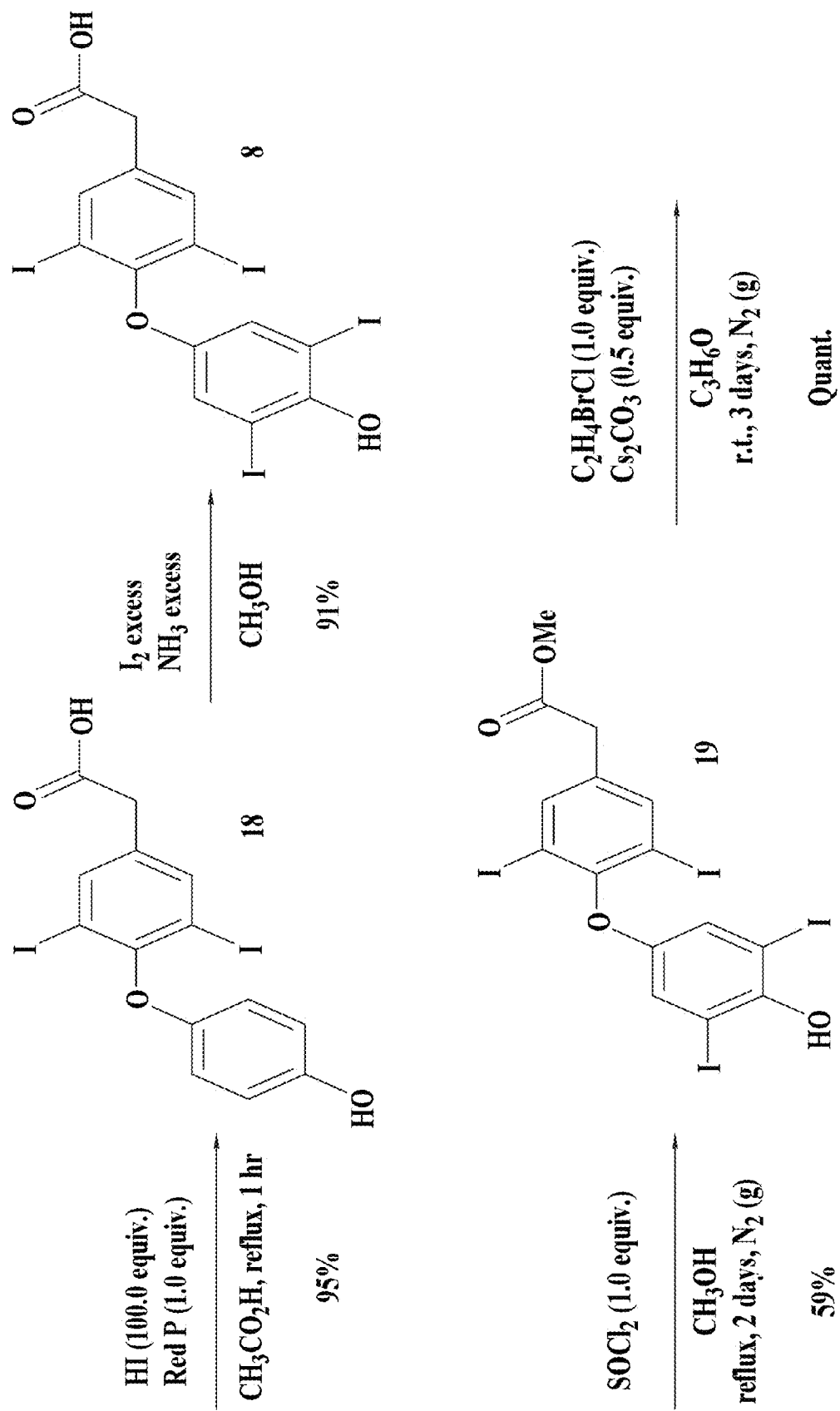
Figure 6C:
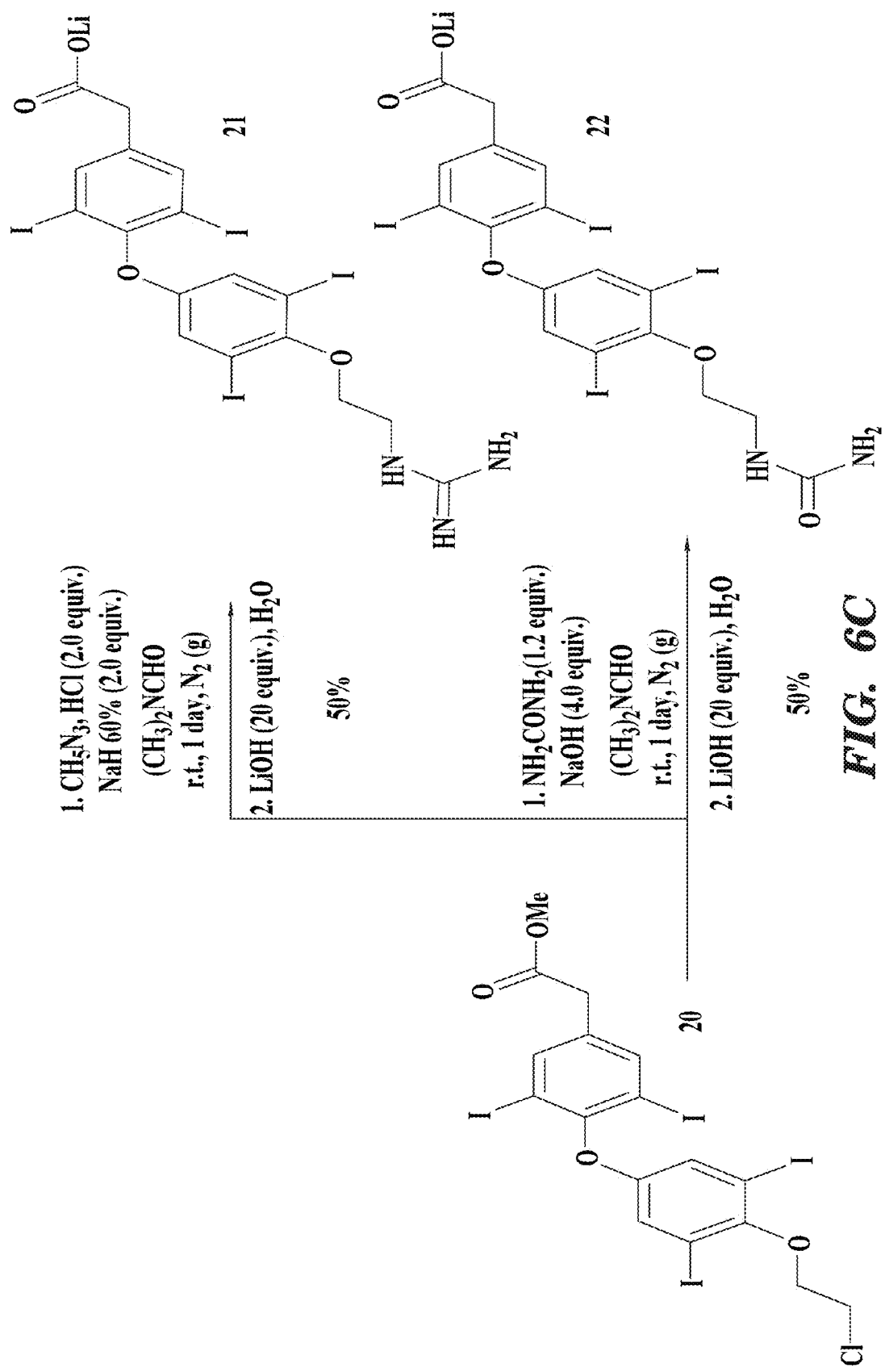
Figure 6D:
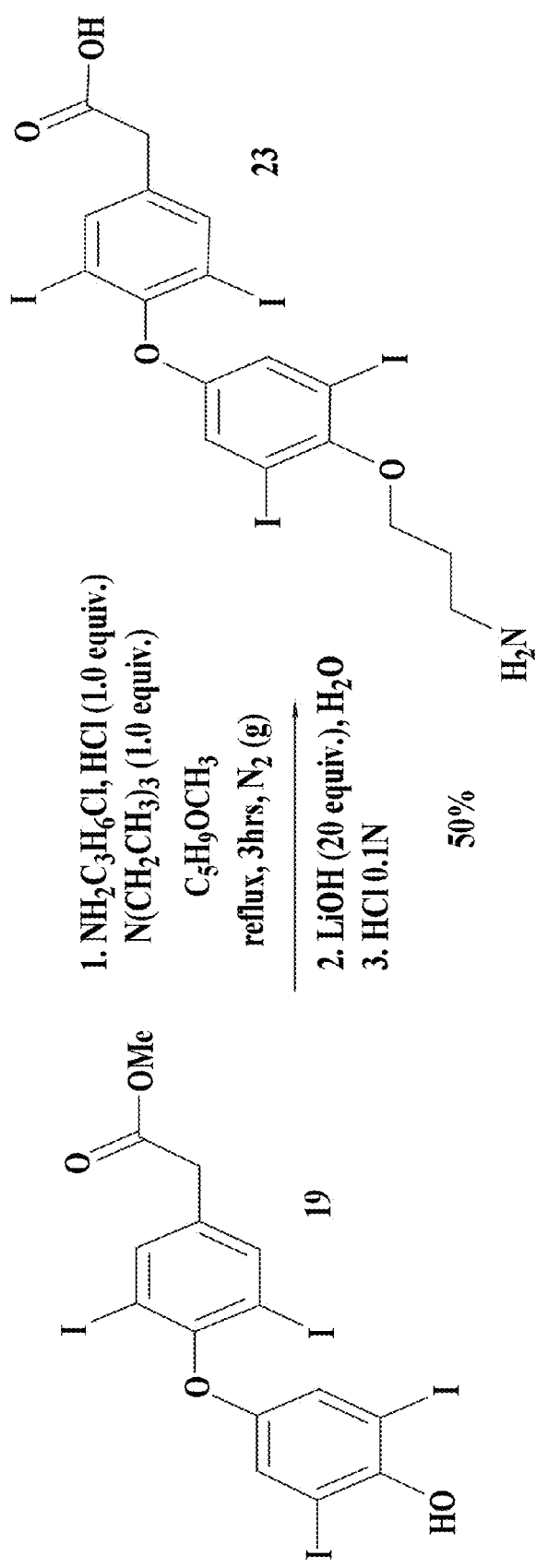

FIG. 5D depicts superimposition of RGDF and XT199 denoting superimposition of the binding orientations of RGDF (white) and XT199 (green), in accordance with embodiments of the present invention.

Analysis of the integrin receptor co-crystallized with a cyclic tripeptide ligand provides valuable insight into this ligand-receptor interaction (FIG. 5A). The cyclic tripeptide occupies a shallow crevice between the propeller and the βA units in the integrin head, with the Arg and Asp residues exclusively contacting the propeller and βA domains, respectively (Asp chelates the metal ion at a distance of 2.6 Å). These interactions with the cyclic tripeptide were used to model the docking of tetrac (FIG. 5B) and XT199 (FIG. 5C) to integrin $\alpha_v\beta_3$. Detailed high resolution images enabled characterization of all potential interactions of each molecule with the integrin receptor. For each compound, the carboxylic acid moiety was mainly responsible for the ligand-receptor interaction, and was involved in the binding of a metal ion (2.6 Å from the metal ion) that occurs only in the active state of the integrin receptor. For XT199, the phenyl sulfonamide moiety stabilized this metal binding by interacting with Arg 214. The interaction of tetrac with the metal ion was stabilized by an electrostatic interaction between vicinal Asn 215 and clear H-bonding between the OH of the phenol group and Tyr 178. XT199 was the only compound that interacted with the Arg recognition site in the propeller domain of $\alpha_v\beta_3$, and the imidazolyl amino group found a best fit between Asp 150 and Asp 218. Superimposition of the structures of XT199 and the cyclic tripeptide ligand showed that the spatial orientation of the entire XT199 molecule was nearly identical to the structure of the Arg-Gly-Asp peptide (FIG. 5D).

To enhance the strength of tetrac as an integrin $\alpha_v\beta_3$ antagonist, the structure was modified to achieve binding to the integrin binding site through both the propeller and the βA domains. Several non-peptide integrin antagonists that function in the nanomolar range were considered, based on reports from several pharmaceutical companies [Mousa S A, Alpha v Vitronectin receptors in vascular-mediated disorders, Med Res Rev. 2003; 23: 190-9; Kerr J S, Slee A M, Mousa S A, The alpha v integrin antagonists as novel anticancer agents: an update. Expert. Opin. Investig, Drugs, 2002; 11: 1765-74], in addition to XT199. The functional groups of interest were an amino pyridine, a guanidine, a urea group and an amine [Henry C, Moitessier N, Chapleur Y, Vitronectin receptor $\alpha_v\beta_3$ integrin antagonists: chemical and structural requirements for activity and selectivity, Mini Rev Med. Chem. 2002; 2: 531-42].

The result was a novel dual Thyrointegrin antagonist (see FIG. 6, described infra). The groups that were added to the structure of tetrac were selected based on their ability to interact with the Arg recognition site in the propeller domain of integrin $\alpha_v\beta_3$. In addition, the distance between the carboxylic acid and the amino group of XT199 impacts activity, so molecules were designed such that this distance was as close to that of XT199 as possible. The length between the amino and the carboxylic acid groups was therefore in harmony with the average interpoint distance defined in blue and red on the three point pharmacophore pattern. Optimization of these dual antagonists has been pursued. Deiodinated Thyrointegrin antagonists with much lower MW value (e.g., MW<500 Da) have been designed as a better alternative to the first analogues.

Preparation of Dual Thyrointegrin Inhibitors

FIGS. 6A, 6B, 6C, and 6D (collectively, "FIG. 6") outline a linear synthetic pathway for the preparation of dual Thyrointegrin inhibitors (chemical structures 21, 22 and 23), in accordance with embodiments of the present invention. The sequential pathway is depicted in FIG. 6 in the sequential order of FIGS. 6A, 6B, 6C, and 6D. Sufficient quantities of tetrac for subsequent modification were generated through a synthesis approach that involved arylation, catalytic reduction, tetrazotization, iodination, esterification, alkylation and hydrolysis. The appropriate starting material, compound 14 in FIG. 6 was prepared by converting commercially available p-hydroxy phenylacetic acid into a dinitro ester in two steps. Nitration followed by acid catalyzed esterification resulted in the desired compound with a 72% yield. Despite the fact that the hydroxyl was prone to oxidation, nitration occurred in a dilute solution of $HNO_3$ in AcOH with minimal side reaction, in comparison to classic nitration in $H_2SO_4$.

A toluene para-sulfonyl derivative of compound 14 was transformed with methoxyphenol in pyridine to give the diphenylether (compound 15) at 75% yield. Catalytic reduction of the nitro groups was carried out quantitatively in ethanol in order to allow the diamino derivative (compound 16) to be tetrazotized at 0° C. The resulting tetrazolium salt was reacted with sodium iodide to give the 3,5-diiodo compound in good yield (compound 17). Due to difficulties with hydrolysis, complete acidolysis of the ester was done under reflux using hydriodic acid (HI) as a strong cleaving agent, which removed both the ester and the O-methyl groups. Acetic acid was added to this reaction instead of $H_2SO_4$ to avoid decomposition of HI into $I_2$. Tetrac (compound 8) was then obtained by two displacements of a proton from the aromatic nucleus of the di-iodoacid (compound 18) by an iodide. In that reaction, the iodo-deprotonation was carried out using $I_2$ in methanolic $NH_3$ in 91% yield. Of note, complete acidolysis of compound 17 revealed some advantage; thereafter aminolysis of the ethyl ester and formation of an amide during the iodination reaction was avoided. Also, selective iodination on the outer ring benefited from the transformation of the methyl ether group into an alcohol. This was done to allow activation of the ortho position by oxygen through inductive and resonance effects.

Acid catalysis of tetrac in MeOH was required to obtain the final Thyrointegrin antagonists (compounds 21, 22 and 23), wherein Me denotes methyl. Thus, tetrac was esterified by acid catalysis in MeOH in 60% yield. The resulting molecule (compound 19) was substituted by a two-carbon polymethylenic chain, and then this intermediate (compound 20) was substituted using guanidine and urea to yield compounds 21 and 22, respectively. Despite the presence in ortho of high radius iodo atoms, the alkylation of the OH group of compound 19 occurred quantitatively with 1-bromo-2-chloroethane under mild conditions. Compound 20 was then reacted with an excess of guanidine after preliminary deprotonation of guanidinium chloride with NaH 60% to give compound 21 (50% yield). Compound 20 was reacted with urea in an anhydrous solution of sodium hydroxide to give compound 22 (50% yield). Other attempts to substitute the chloride of compound 20, for example by using 2-aminopyridine, ammonia or dilute ammonia in an alcohol solution, were unsuccessful. Direct substitution of the OH of the phenol of compound 19 with chloroethylamine and other substrates containing an amine with longer polymethylene chains was also unsuccessful. Compound 23, the only compound with a single amino group, was obtained with a yield of 47% after refluxing compound 19 with chloropropylamine hydrochloride in an environmentally-friendly solvent, cyclopentyl methyl ether. Finally, isolated 21, 22 and 23 were hydrolyzed using an excess of aqueous LiOH (compounds 21 and 22) or aqueous NaOH (compound 23).

Figure 7A:
FIGS. 7A, 7B, and 7C depict molecular modelling of the binding of Thyrointegrin antagonists to the integrin receptor for the dual Thyrointegrin inhibitors synthesized in FIG. 6, in accordance with embodiments of the present invention.
Figure 7B:
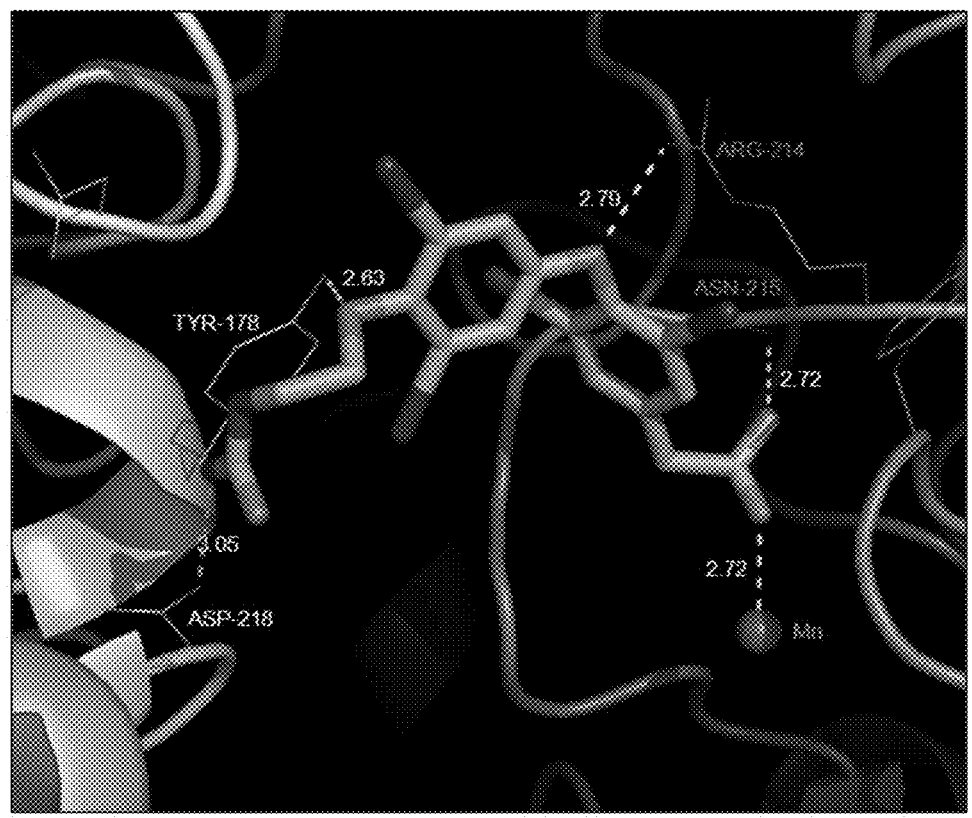
Figure 7C:
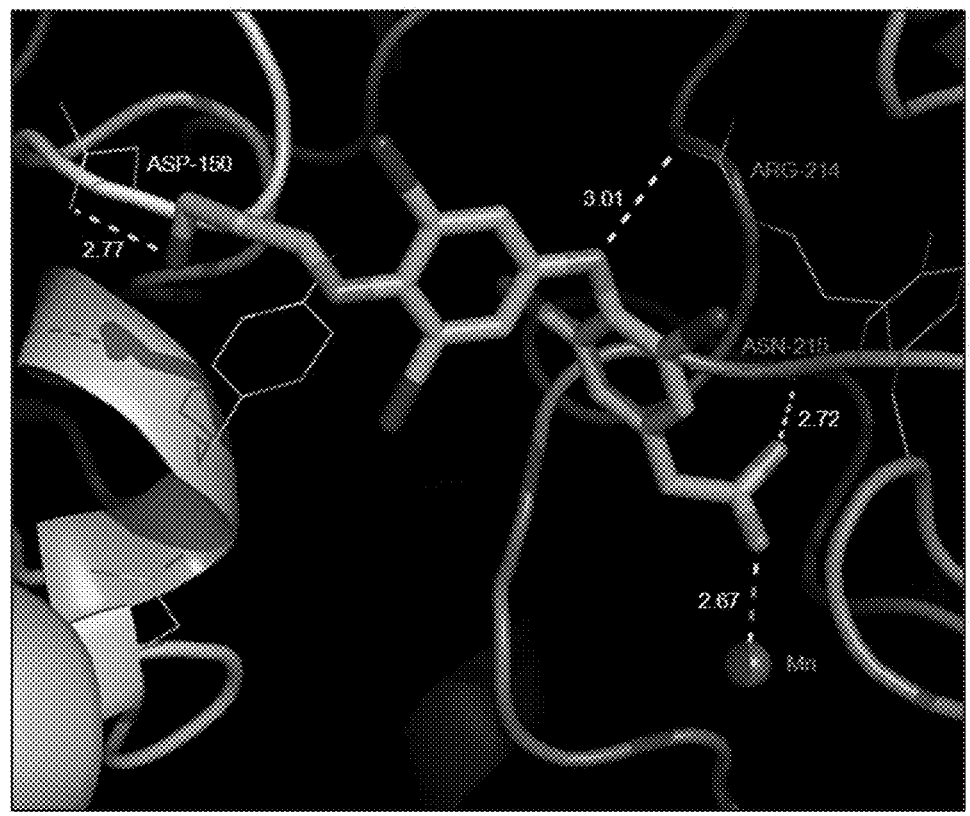

FIGS. 7A, 7B, and 7C depict molecular modelling of the binding of Thyrointegrin antagonists to the integrin receptor for the dual Thyrointegrin inhibitors synthesized in FIG. 6, in accordance with embodiments of the present invention. Compound 21 (FIG. 5A), compound 22 (FIG. 5B), and compound 23 (FIG. 5C), all in green, are bound at the interface of the αvβ3 integrin αv-subunit (yellow) and βA domain (purple). The blue ball represents the manganese ion and yellow dotted lines illustrate H-bond interactions.

Figure 8:
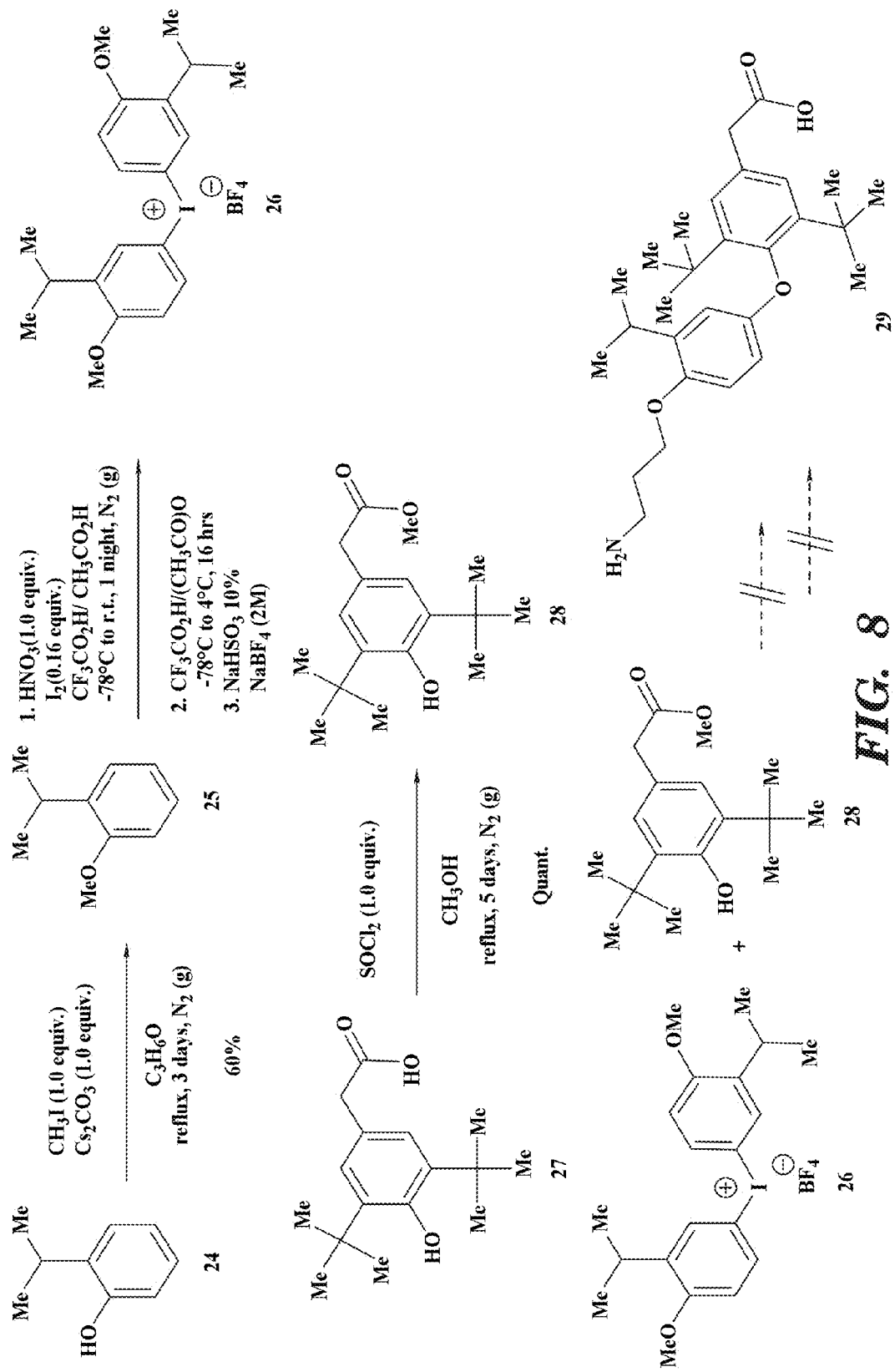
FIG. 8 outlines a linear synthetic pathway for the preparation of a deiodinated compound, in accordance with embodiments of the present invention.

FIG. 8 outlines a linear synthetic pathway intended for the preparation of a deiodinated compound having a molecule with the same distance between the carboxylic and amino groups as that of XT199, in accordance with embodiments of the present invention. The critical step in the synthesis (FIG. 4) was the condensation of starting materials 26 and 28. Compound 28 was obtained quantitatively by thionyl chloride catalyzed esterification of 3,5-di-tert-butyl-4-hydroxybenzoic acid (compound 27). The intent was to couple the compounds after the formation of the bis aryliodonium triflate (compound 26) prepared following the method of Yokoyama et al. [Yokoyama N, Walker G N, Main A J, Stanton J L, Morrissey MM, Boehm C, Engle A, Neubert A D, Wasvary J M, Stephan Z F, Steele R E, Synthesis and structure-activity relationships of oxamic acid and acetic acid derivatives related to L-thyronine, J Med. Chem. 1995; 38: 695-707]. However, upon treatment with tetrafluoroborate salt, instead of a precipitate, only an unusable red solution in the flask was obtained.

Chemical Structures

In one embodiment, the dual thyrointegrin antagonist of the present invention is a compound having the chemical structure depicted in FIG. 1.

In one embodiment, the dual thyrointegrin antagonist of the present invention is a compound having the following chemical structure 41:

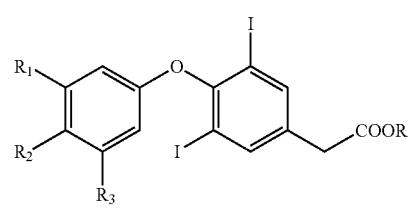

41

In one embodiment for the chemical structure 41, $R_1$ is iodine, hydrogen, hydroxy, or aminoalkyl containing 3 to 5 carbon atoms.

In one embodiment for the chemical structure 41, $R_2$ is iodine, hydrogen, hydroxyl and aminoalkyl containing 3 to 5 carbon atoms; t-Boc aminoalkyloxyl, aminoalkyloxyl containing 3 to 5 carbon atoms, including free base or corresponding HCl salt; N-(3-pyrridin-methyl) amino alkyloxyl containing 3 to 5 carbon atoms, including free base or corresponding HCl salt; thiomorpholin-yl alkyloxyl containing 3 to 5 carbon atoms, including free base or corresponding HCl salt; diethylaminoalkyloxyl containing 3 to 5 carbon atoms, including free base or corresponding HCl salt; or 1,2-dimethylpropylaminoalkyloxyl containing 3 to 5 carbon atoms, including free base or corresponding HCl salt.

In one embodiment for the chemical structure 41, $R_3$ is iodine, hydrogen, hydroxyl, or aminoalkyl containing 3 to 5 carbon atoms.

In one embodiment for the chemical structure 41, R is hydrogen, methyl, ethyl, propyl, isopropyl, etc. as a prodrug.

In one embodiment, the chemical structure 41 has the following characteristics:

R is selected from the group consisting of hydrogen, methyl, ethyl, propyl, and isopropyl;
  wherein a group X is —$(CH_2)_nNH_2$ such that n is 3, 4, or 5;
  wherein a first condition, a second condition, a third condition, a fourth condition, or a fifth condition is satisfied;
  wherein the first condition is that ($R_1$ is X, $R_2$ is I, and $R_3$ is I), ($R_1$ is I, $R_2$ is X, and $R_3$ is I), or ($R_1$ is I, $R_2$ is I, and $R_3$ is X);
  wherein the second condition is that $R_1$, $R_2$, and $R_3$ are each selected from the group consisting of X, H, and I such that $R_1$, $R_2$, and $R_3$ differ from each other;
  wherein the third condition is that $R_1$, $R_2$, and $R_3$ are each selected from the group consisting of X, OH, and I such that $R_1$, $R_2$, and $R_3$ differ from each other;
  wherein the fourth condition is that $R_1$, $R_2$, and $R_3$ are each selected from the group consisting of X, OH, and H such that $R_1$, $R_2$, and $R_3$ differ from each other; and
  wherein the fifth condition is that $R_1$ is I, $R_3$, is I, and $R_2$ is selected from the group consisting of t-BocNCH$_2$CH$_2$CH$_2$O—, HCl NH$_2$CH$_2$CH$_2$CH$_2$O—,

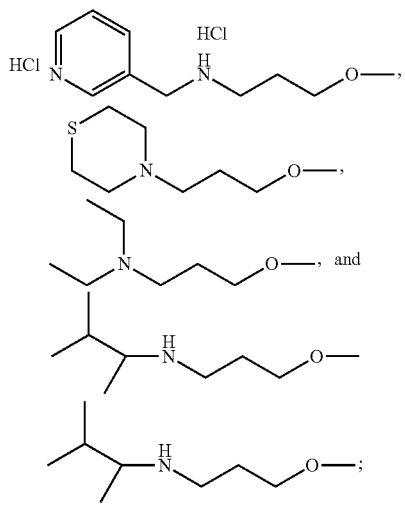

and
wherein t-Boc stands for tert-Butyloxycarbonyl.

Various combinations of R, R$_1$, R$_2$, and R$_3$ for the chemical structure 41 are presented in the table depicted in Appendix A.

In one embodiment, the dual thyrointegrin antagonist of the present invention is a compound having the following chemical structure 42:

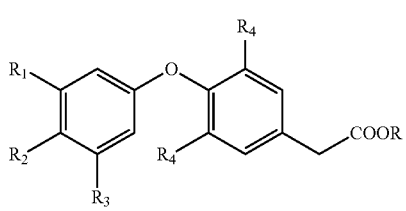

42

In one embodiment for the chemical structure 42, R is methyl, ethyl, propyl, isopropyl, etc as a prodrug.

In one embodiment for the chemical structure 42, R$_1$ is iodine; hydroxyl; aminoalkyl containing 3 to 5 carbon atoms; guanidineylethyl; ureaylethyl; hydroxyaminoethyl; isopropyl; 2-pyridinylethenyl; 3-pyridinylethenyl; or 4-pyridinylethenyl.

In one embodiment for the chemical structure 42, R$_2$ is iodine; hydroxyl; aminoalkyl containing 3 to 5 carbon atoms; guanidineylethyl; ureaylethyl; hydroxyaminoethyl; isopropyl; 2-pyridinylethenyl; 3-pyridinylethenyl; or 4-pyridinylethenyl.

In one embodiment for the chemical structure 42, R$_3$ is iodine; hydroxyl; aminoalkyl containing 3 to 5 carbon atoms; guanidineylethyl; ureaylethyl; hydroxyaminoethyl; isopropyl; 2-pyridinylethenyl; 3-pyridinylethenyl; or 4-pyridinylethenyl.

In one embodiment for the chemical structure 42, R$_4$ is iodine, bromine, methyl, t-butyl, etc.

In one embodiment, the chemical structure 42 has the following characteristics:

wherein R is selected from the group consisting of hydrogen, methyl, ethyl, propyl, and isopropyl;

wherein a group Y is selected from the group consisting of
OH,
—(CH$_2$)$_n$NH$_2$ such that n is 3, 4, or 5,

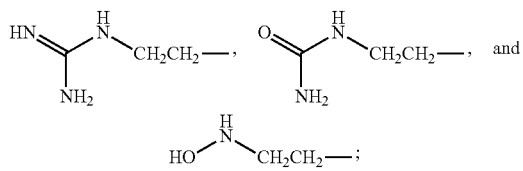

wherein a group R$_5$ is

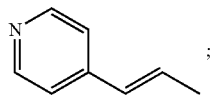

wherein a group R$_6$ is

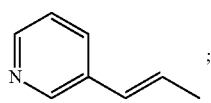

wherein a group R$_7$ is

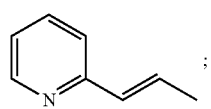

wherein a group R$_8$ is

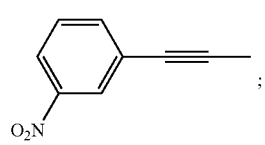

wherein a group R$_9$ is

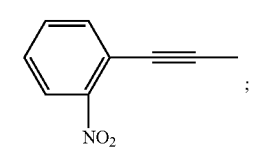

wherein a group R$_{10}$ is selected from the group consisting of R$_5$, R$_6$, and R$_7$;
wherein a group R$_{11}$ is selected from the group consisting of R$_8$ and R$_9$;
wherein a first condition, a second condition, a third condition, a fourth condition, or a fifth condition is satisfied;
wherein the first condition is that (R$_1$ is I, R$_2$ is Y, R$_3$ is I, and R$_4$ is I), (R$_1$ is Y, R$_2$ is I, R$_3$ is I, and R$_4$ is I), or (R$_1$ is I, R$_2$ is I, R$_3$ is Y, and R$_4$ is I);

wherein the second condition is that ($R_1$ is i-Pr, $R_2$ is Y, $R_3$ is i-Pr, and $R_4$ is Br), ($R_1$ is Y, $R_2$ is i-Pr, $R_3$ is i-Pr, and $R_4$ is Br), or ($R_1$ is i-Pr, $R_2$ is i-Pr, $R_3$ is Y, and $R_4$ is Br);

wherein the third condition is that $R_4$ is Br and that $R_1$, $R_2$, and $R_3$ are each selected from the group consisting of Y, i-Pr, and $R_{10}$ such that $R_1$, $R_2$, and $R_3$ differ from each other;

wherein the fourth condition is that $R_4$ is methyl and that $R_1$, $R_2$, and $R_3$ are each selected from the group consisting of Y, i-Pr, and $R_{11}$ such that $R_1$, $R_2$, and $R_3$ differ from each other;

wherein the fifth condition is that $R_4$ is t-butyl and that $R_1$, $R_2$, and $R_3$ are each selected from the group consisting of Y, i-Pr, and H such that $R_1$, $R_2$, and $R_3$ differ from each other;

wherein i-PR stands for isopropyl.

Various combinations of R, $R_1$, $R_2$, $R_3$, and $R_4$ for the chemical structure 42 are presented in the table depicted in Appendix B.

Biological Evaluation: Angiogenesis in the Cam Model

To investigate the structure-activity relationships of novel dual Thyrointegrin inhibitors of the present invention, the effect of each compound on angiogenesis-induced by the growth factor basic fibroblast growth factor (FGF) was assessed in the CAM model as depicted in Table 1.

TABLE 1

Inhibition of angiogenesis by novel dual thyrointegrin antagonists in CAM model

| Treatment | Mean % inhibition |
|---|---|
| FGF + XT-199 (5 µg/ml) | 86 ± 09 |
| FGF + Tetrac (10 µg/ml) | 85 ± 11 |
| FGF + 21 (0.25 µg/ml) | 75 ± 10 |
| FGF + 22 (0.25 µg/ml) | 74 ± 13 |
| FGF + 23 (0.25 µg/ml) | 88 ± 11 |
| FGF + 29 (0.25 µg/ml) | 83 ± 08 |

The data in Table 1 represents a mean±standard deviation (SD), n=8 as compared to FGF alone (p<0.001; 10 µl from the different test compounds were added to the FGF impregnated sterile filter).

EXAMPLE

Angiogenesis in the Chick Chorioallantoic Membrane Model

The CAM system is a widely-used model in which the chick embryonic membrane is exposed to stimulatory and inhibitory compounds. Ten day-old fertilized chicken eggs (Sunrise Farms Inc, Catskill, N.Y.) were incubated at 37° C. and 55% relative humidity. In the dark, with the help of a candling lamp, a small hole was punctured in the area of the shell covering the air sac using a hypodermic needle. A second hole was punctured on the wider side of the egg above an avascular area of the embryonic membrane. An artificial air sac was created below the second hole by gently applying a vacuum to the first hole using a small rubber squeeze bulb. The vacuum caused the separation of the CAM from the shell. A window of approximately 1.0 cm$^2$ was cut in the shell over the dropped CAM with the use of a mini drill. The underlying CAM was accessed through this small window. Filter disks were punched from filter paper #1 (Whatman International, Ltd, United Kingdom), and then soaked in 3.0 mg/mL cortisone acetate solution (in 95% ethanol) and air-dried under sterile conditions. To induce angiogenesis, sterile filter disks were saturated with FGF and placed on the CAM using sterile forceps. As a control, disks were saturated with PBS without calcium or magnesium. The window was sealed with Highland Brand transparent tape. After 1 hour, 10 µL of inhibitor were applied topically to the FGF-stimulated CAM. After 48 hours, CAM tissue directly beneath the filter disk was harvested and placed in a 35-mm petri dish for evaluation of angiogenesis. Eight eggs were used per treatment.

Digital Imaging and analysis: CAMs in petri dishes were examined using a SV6 stereomicroscope (Carl Zeiss Microlmaging, Inc) at 50× magnification. Digital images were captured using a 3-CCD color video camera system (Toshiba America, Inc, New York, N.Y.). The images were analyzed using Image-Pro Plus (Media Cybernetics, Inc). The number of branch points within a circular region superimposed on the area of the filter disk was counted for each treatment condition.

All compounds exhibited strong in vivo anti-angiogenic activity, with an average of 63-75% inhibition even at low doses (Table 2) as compared to know potent αvβ3 antagonist, XT199 (Table 1).

TABLE 2

Anti-angiogenesis efficacy of additional thyrointegrin antagonists in CAM model

Thyrointegrin Antagonists Compounds

| Code | MF | Mean % Inhibition of Angiogenesis | Structure* | Mean % Inhibition of αvβ3 Binding |
|---|---|---|---|---|
| 30 | $C_{22}H_{23}I_4NO_6$ | 75 ± 07 | 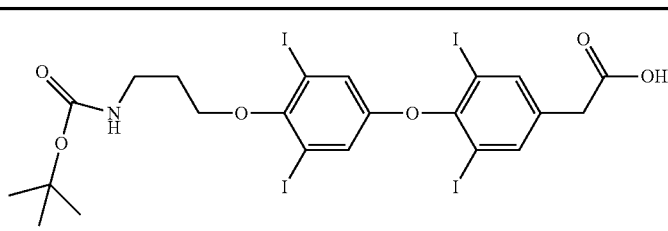 | 66 ± 8 |

TABLE 2-continued

Anti-angiogenesis efficacy of additional thyrointegrin antagonists in CAM model

Thyrointegrin Antagonists Compounds

| Code | MF | Mean % Inhibition of Angiogenesis | Structure* | Mean % Inhibition of $\alpha v\beta 3$ Binding |
|---|---|---|---|---|
| 31 | $C_{18}H_{18}ClI_4NO_4$ | 0.0 ± 0.0 | 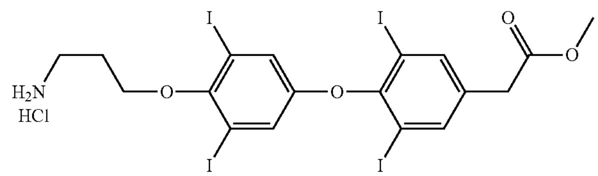 [SMILES: Cl ; COC(=O)Cc1cc(I)c(Oc2cc(I)c(OCCCN)c(I)c2)c(I)c1] | 0.0 ± 0.0 |
| 32 | $C_{17}H_{16}ClI_4NO_4$ | 88 ± 08 | 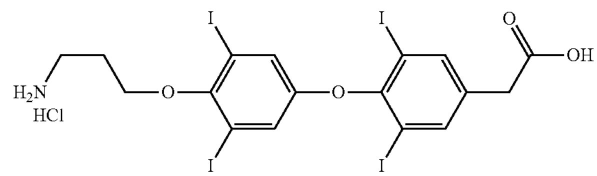 [SMILES: Cl ; NCCCOc1c(I)cc(Oc2c(I)cc(CC(=O)O)cc2I)cc1I] | 100 ± 00 |
| 33 | $C_{24}H_{24}Cl_2I_4N_2O_4$ | 0.0 ± 0.0 | 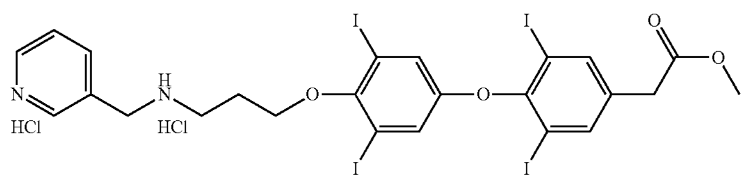 [SMILES: COC(=O)Cc1cc(I)c(Oc2cc(I)c(OCCCNCc3cccnc3)c(I)c2)c(I)c1 ; Cl ; Cl] | 0.0 ± 0.0 |
| 34 | $C_{23}H_{22}Cl_2I_4N_2O_4$ | 95 ± 11 | 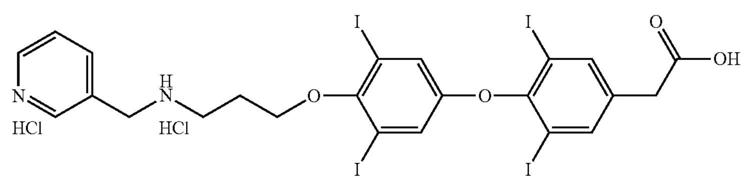 [SMILES: O=C(O)Cc1cc(I)c(Oc2cc(I)c(OCCCNCc3cccnc3)c(I)c2)c(I)c1 ; Cl ; Cl] | 68 ± 07 |
| 35 | $C_{22}H_{23}I_4NO4S$ | 0.0 ± 0.0 | 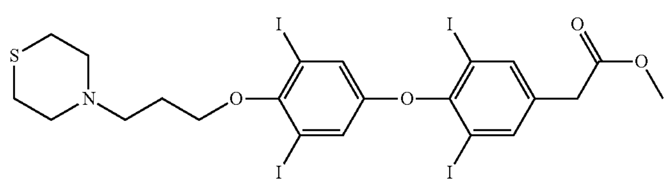 [SMILES: COC(=O)Cc1cc(I)c(Oc2cc(I)c(OCCCN3CCSCC3)c(I)c2)c(I)c1] | 0.0 ± 0.0 |
| 36 | $C_{21}H_{21}I_4NO_4S$ | 89 ± 10 | 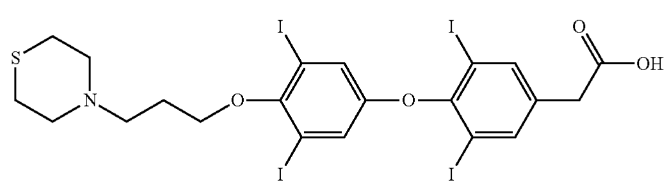 [SMILES: O=C(O)Cc1cc(I)c(Oc2cc(I)c(OCCCN3CCSCC3)c(I)c2)c(I)c1] | 93 ± 08 |
| 37 | $C_{22}H_{25}I_4NO_4$ | 0.0 ± 0.0<br>83 ± 06 | 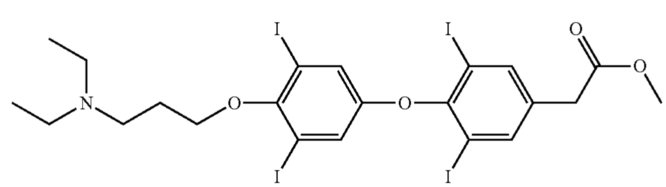 [SMILES: CCN(CC)CCCOc1c(I)cc(Oc2c(I)cc(CC(=O)OC)cc2I)cc1I] | 1.0 ± 0.0<br>100 ± 00 |

*Structure modifications with either Tetra iodo (Tetrac analogues) or Tri-iodo (Triac analogues); 10 μl from the different test compounds at 0.25 mg/ml were added to the FGF impregnated sterile filter; Anti-avb3 (Inhibition of $\alpha v\beta 3$-medited binding in a specific cell adhesion assay at 100 nM).
**Anti-angiogenesis and anti-$\alpha v\beta 3$ binding post-ester hydrolysis to make the free acid These results provided an important foundation for further experiments on the effects of these novel antagonists. To that end, FlexX was used to model putative ligand-receptor interactions of the three novel dual Thyrointegrin antagonists with integrin $\alpha_v\beta_3$ (FIGS. 7A-C). The interactions predicted by FlexX have kept with the strict requirements defined in the pattern of $\alpha_v\beta_3$ antagonists. First, both guanidinium and its bioisostere urea have interacted with Asp218 (on $\alpha_v$). Due to the longer linker chain, the amino group of compound 23 has interacted with Asp150, located deeper in $\alpha_v$. Second, the acetic acid end of all compounds has fitted in the same short narrow pocket filled by the manganese ion as tetrac did. These pictures compelled consideration of deeper the investigation of the deiodinated dual antagonists with other methods which have shown to reflect the situation in the whole organism; e.g., the crosstalk interaction between the integrin $\alpha_v\beta_3$ and the TRs.

EXAMPLES

Chemistry

All commercially available chemicals were used without further purification. All solvents were dried, and moisture-sensitive reactions were performed under dry nitrogen. Analytical TLC was performed on pre-coated Kieselgel 60F$_{254}$ plates (Merck). Analytical RPTLC was performed on pre-coated Kieselgel plates (Merck). Compounds were visualized by UV and/or with iodine. Column chromatography was performed with silica gel Kieselgel Si 60, 0.040-0.063 mm (Merck). Melting points were determined on an Electro thermal MEL-TEMP melting point apparatus and then on a Thomas Hoover Uni-melt capillary melting point apparatus and were not corrected. The structures of all compounds were supported by infrared spectra recorded on a Thermo Electron Nicolet Avatar 330 FT-IR apparatus. UV spectra were obtained from a Shimadzu UV-1650 (PC) UV-vis spectrophotometer. $^1$H NMR data were obtained using a Varian Inova 500 MHz spectrometer and referenced to CDCl$_3$ ($\delta$=7.27 ppm) or DMSO-d6 ($\delta$=2.50 ppm). High Resolution Mass Spectral analyses were obtained on either Applied Biosystems API4000 LC/MS/MS or Applied Biosystems QSTAR XL mass spectrometers. $^1$H NMR chemical shifts were reported in ppm downfield from tetramethylsilane, J values were in Hertz and the splitting patterns were designated as follows: s, singlet; d, doublet; dd, doublet of doublets; t, triplet; q, quartet; m, multiplet; b, broad. HPLC experiments were carried out at a flow rate of 1.1 mL·minute$^{-1}$ with a Waters 2695 HPLC apparatus (120 vials) and a Phenomenex Luna® 5 u NH$_2$ 100 A or a Waters µBondapak® C18 10 µm 125 A column operated at 40° C. and atmospheric pressure with UV detection between 210 and 400 nm. Refractive index was measured with an Abbe 3L Refractometer with bromonaphtalene as the contact liquid. Combustion analyses were performed by Intertek, Inc, Whitehouse, N.J. The yields quoted in this paper were re-crystallization yields.

[4-(4-Hydroxy-3,5-diiodophenoxy)-3,5-diiodophenyl]acetic acid (8)

The title compound was prepared as described by Wilkinson J H Synthesis of some Possible Metabolites of Thyroxin and Triiodothyronine Biochem J. 1956 August; 63(4):601-605.

Methyl [4-(4-hydroxy-3,5-diiodophenoxy)-3,5-diiodophenyl]acetate (19)

[4-(4-Hydroxy-3,5-diiodophenoxy)-3,5-diiodophenyl] acetic acid (5.0 g, 6.7 mmol, 1.0 equiv.) was dissolved in 200 mL of dried MeOH. Then thionyl chloride (485 µL, 6.7 mmol, 1.0 equiv.) was added drop wise. The reaction was set to reflux for 2 days. Water was then added to the reaction medium (200 mL) and then the solution was concentrated. The precipitated product was collected by filtration and then the aqueous phase analyzed by TLC but showed to contain no product. The solid was then re-crystallized in EtOH, filtered and washed with cold EtOH before being dried under vacuum.

Yield: Quantitative, white powder; recrystallization solvent: EtOH; TLC: 0.81 (DCM); RPTLC: 0.49 (AcOH/H$_2$O 90/10); mp=163° C.; IR ($\nu$ cm$^{-1}$): 1719; UV (DMSO): $\lambda_{max}$ nm=225; HPLC (µBondapak C18): rt=3.2 minutes (MeOH/H$_2$O 65/35); $^1$H NMR (CDCl$_3$) $\delta$ (ppm): 7.78 (s, 2H, ArH), 7.12 (s, 2H, ArH), 5.53 (br, 1H, OH), 3.75 (s, 3H, CH$_3$), 3.58 (s, 2H, CH$_2$); $^{13}$C NMR (CDCl$_3$) $\delta$ (ppm): 152.8, 150.2, 149.6, 142.3, 135.2, 126.9, 125.3, 91.0, 81.9, 52.3, 39.3.

Methyl {4-[4-(2-chloro ethoxy)-3,5-diiodophenoxy]-3,5-diiodophenyl}acetate(20)

Methyl [4-(4-hydroxy-3,5-diiodophenoxy)-3,5-diiodophenyl]acetate (2.4 g, 3.2 mmol, 1 equiv.) was dissolved in anhydrous acetone, cesium carbonate was then added (522 mg, 1.6 mmol, 0.5 equiv.) and then 1-bromo-2-chloroethane (275 µL, 3.2 mmol, 1.0 equiv.) was added drop wise. After stirring for 3 days at room temperature (r.t.), the medium was filtered over Celite and the residue was evaporated to give a yellow powder.

Yield: Quantitative, white powder; recrystallization solvent: EtOH; TLC: 0.76 (DCM); mp=119° C.; IR ($\nu$ cm$^{-1}$): 1732; UV (DMSO): $\lambda_{max}$ nm=256; HPLC (µBondapak C18): rt=4.7 minutes (MeOH/H$_2$O 70/30); $^1$H NMR (CDCl$_3$) $\delta$ (ppm): 7.75 (s, 2H, ArH), 7.15 (s, 2H, ArH), 4.19 (t, J=5.5 Hz, 2H, CH$_2$), 3.91 (t, J=5.5 Hz, 2H, CH$_2$), 3.72 (s, 3H, CH$_3$), 3.55 (s, 2H, CH$_2$); HRMS (APCI) m/z: 823.6 [(M)$^+$, 100]; Analytical (C$_{17}$H$_{13}$ClI$_4$O$_4$) C: calcd, 24.77. found, 24.98, H: calcd, 1.59. found, 1.52.

Lithium [4-(4-{2-[(diaminomethylene)amino] ethoxy}-3,5-diiodophenoxy)-3,5-diiodophenyl]acetate (21)

To a solution of methyl {4-[4-(2-chloroethoxy)-3,5-diiodophenoxy]-3,5-diiodophenyl}acetate (200 mg, 0.2 mmol, 1.0 equiv.) in anhydrous DMF (5 mL) was added drop wise a mixture of sodium hydride (60% dispersion in mineral oil; 19 mg, 0.5 mmol, 2.0 equiv.) and guanidine hydrochloride (45.8 mg, 0.5 mmol, 2.0 equiv.) in DMF (5 mL). After stirring for 1 day at r.t., the medium was hydrolyzed with a solution of LiOH (115 mg, 4.9 mmol, 20.0 equiv.). The precipitate was then filtered from hot EtOH.

Yield: 50%, white powder; TLC: 0.12 (EtOH); mp=133° C.; IR ($\nu$ cm$^{-1}$): 1736; UV (DMSO): $\lambda_{max}$ nm=256; HPLC (µBondapak C18): rt=6.06 minutes (MeOH/H$_2$O 65/35); $^1$H NMR (CD$_3$OD) $\delta$ (ppm): 7.88 (s, 2H, ArH), 7.19 (s, 2H, ArH), 4.20 (t, J=5.5 Hz, 2H, CH$_2$), 3.91 (t, J=5.5 Hz, 2H, CH$_2$), 3.45 (s, 2H, CH$_2$); $^{13}$C NMR (CDCl$_3$) $\delta$ (ppm): 206.9, 171.5, 153.2, 152.7, 151.8, 141.5, 136.7, 126.0, 92.0, 91.8, 72.9, 52.3, 43.8, 38.1; HRMS (APCI) m/z: 841.7 [(M+3H+Li)$^+$, 100].

(4-{4-[2-(Carbamoylamino)ethoxy]-3,5-diiodophenoxy}-3,5-diiodophenyl)acetic acid(22)

To a solution of methyl {4-[4-(2-chloroethoxy)-3,5-diiodophenoxy]-3,5-diiodophenyl}acetate (1.5 g, 1.8 mmol, 1.0 equiv.) in anhydrous DMF (15 mL) was added drop wise a mixture of sodium hydroxide (285 mg, 7.1 mmol, 4.0 equiv.) and urea (107 mg, 1.8 mmol, 1.0 equiv.) in anhydrous DMF (5 mL). After stirring for 1 day at r.t., the medium was hydrolyzed with a solution of LiOH (504 mg, 21.0 mmol, 12.0 equiv.). The precipitate was then filtered from hot EtOH.

Yield: 50%, light brown powder; TLC: 0.77 (DCM); RPTLC: 0.5 (AcOH); mp=267° C.; IR (ν cm$^{-1}$): 1735; UV (DMSO): $\lambda_{max}$ nm=256; HPLC (µBondapak C18): rt=3.85 minutes (MeOH/H$_2$O 60/40); $^1$H NMR (CD$_3$OD) δ (ppm): 7.88 (s, 2H, ArH), 7.19 (s, 2H, ArH), 4.19 (t, J=5.5 Hz, 2H, CH$_2$), 3.95 (t, J=5.5 Hz, 2H, CH$_2$), 3.45 (s, 2H, CH$_2$); HRMS (APCI) m/z: 832.6 [(M)$^+$, 100], 834.6 [(M+H)$^+$, 34]; Analytical (C$_{17}$H$_{14}$I$_4$N$_2$O$_5$) C: calcd, 24.48. found, 24.57; H: calcd, 1.69. found, 1.59.

{4-[4-(3-aminopropoxy)-3,5-diiodophenoxy]-3,5-diiodophenyl}acetic acid (23)

Methyl {4-[4-(2-chloroethoxy)-3,5-diiodophenoxy]-3,5-diiodophenyl}acetate (2.5 g, 3.3 mmol, 1.0 equiv.) was dissolved in cyclopentyl methyl ether then triethylamine (460 µL, 3.3 mmol, 1.0 equiv.) was added together with chloropropylamine (427 mg, 3.3 mmol, 1.0 equiv.). After refluxing the reaction medium for 3 hrs, the solvent was evaporated and water was added to the residue to which was added LiOH solution (1.6 g, 66.0 mmol, 20.0 equiv.). The obtained powder was filtered and washed by hot MeCN and then by hot EtOH.
The product was characterized after filtration and drying.

Then to test the compound in a biological assay, water was added to the obtained salt (5 mL) and a solution of HCl 0.1 N (5.0 mL) was added drop wise, after filtration, the product was obtained as a white powder (668 mg). NaOH 1.0 N (280 mg, 6.6 mmol, 2.0 equiv.) was then added drop by drop to the powder and the product was filtered again and then re-crystallised in EtOH.

Yield: 47%, white powder; mp>250° C.; IR (ν cm$^{-1}$): 1697; UV (DMSO): $\lambda_{max}$ nm=259; HPLC (µBondapak C18): rt=17.5 minutes (Ammonium acetate 25 mM pH4/MeOH 50/50); $^1$H NMR (Acetone-d6) δ (ppm): 7.99 (s, 2H, ArH), 7.30 (s, 2H, ArH), 4.27 (t, J=5.5 Hz, 2H, CH$_2$), 3.95 (t, J=5.5 Hz, 2H, CH$_2$), 3.75 (s, 2H, CH$_2$), 3.57 (q, J=14.0 Hz, J=7.0 Hz, 2H, CH$_2$); HRMS (APCI) m/z: 832.6 [(M−2H+ Li+Na)$^+$, 100]; HRMS (APCI) m/z: 764.7 [(M−COOH+Li)$^-$, 100]; Analytical (C$_{17}$H$_{14}$I$_4$LiNO$_4$) C: calcd, 25.18. found, 24.87; H: calcd, 1.74. found, 1.53.

2-isopropyl anisole (25)

The title compound was prepared with minor variations from the protocol described by Baxter, J., Goede, P., Apriletti, J., et al. (2002). Structure-Based Design and Synthesis of a Thyroid Hormone Receptor (TR) Antagonist. *Endocrinology*, 143 (2), 517-524.

Yield: 60%, yellow oil; TLC: 0.65 (cyclohexane/EtOAc (95/5)); $^1$H NMR (CDCl$_3$) δ (ppm): 7.32-7.30 (dd, J=8.0 Hz, J=2.5 Hz, 1H, ArH), 7.27-7.23 (dt, J=9.5 Hz, J=2.0 Hz, 1H, ArH), 7.04-7.01 (dt, J=7.5 Hz, J=1.0 Hz, 1H, ArH), 6.94-6.92 (dd, J=8.0 Hz, J=1.0 Hz, 1H, ArH), 3.90 (s, 3H, CH$_3$), 3.47-3.41 (m, 1H, CH), 1.30 (s, 3H, CH$_3$), 1.20 (s, 3H, CH$_3$); n$_{[D]}^{20}$: 1.5069.

{4-[4-(3-aminopropoxy)-3,5-diiodophenoxy]-3,5-diiodophenyl}acetic acid (26)

The title compound was prepared as described by Yokoyama N, Walker G N, Main A J, Stanton J L, Morrissey MM, Boehm C, Engle A, Neubert A D, Wasvary J M, Stephan Z F, Steele R E. Synthesis and structure-activity relationships of oxamic acid and acetic acid derivatives related to L-thyronine. J Med. Chem. 1995; 38: 695-707.

methyl (3,5-di-tert-butyl-4-hydroxyphenyl) acetate (28)

15.0 g (56.7 mmol) of 2,6-di-tert-butyl-4-hydroxyphenylacetic acid were dissolved in 100 mL of dried MeOH. Then thionyl chloride (4.11 mL; 56.7 mmol) was added drop wise. The reaction was set to reflux for 5 days. Water was then added to the reaction medium (200 mL) and then the solution was concentrated. The precipitated product (≈20 g) was collected by filtration and then the aqueous phase was extracted 3 times by EtOAc. The organic phases were collected and then dried over MgSO$_4$. The solid was then re-crystallized in EtOH, filtered and washed with cold EtOH.

Yield: quantitative, clear crystals; mp: 88° C.; TLC: 0.81 (DCM); RPTLC: 0.78 (AcOH); IR (ν cm$^{-1}$): 1722; UV (DMSO): $\lambda_{max}$ nm=276; HPLC (µBondapak C18): rt=4.0 minutes (MeOH/H$_2$O 65/35); $^1$H NMR (CDCl$_3$) δ (ppm): 7.14 (s, 2H, ArH), 3.75 (s, 2H, CH$_2$), 3.60 (s, 2H, CH$_2$), 1.50 (s, 18H, CH$_3$); $^{13}$C NMR (CDCl$_3$) δ (ppm172.9, 153.2, 136.2, 126.9, 125.3, 124.9, 53.3, 51.7, 51.0, 41.2, 40.1, 34.5, 32.4, 31.2, 29.9, 28.5; Analytical (C$_{17}$H$_{26}$O$_3$) C: calcd, 73.34. found, 73.39; H: calcd, 9.41. found, 9.27.

EXAMPLE

Mouse Matrigel Model of Angiogenesis

Matrigel Study: Normal male mice (C57BL/6NCr) 6-8 weeks of age and weighing ~20 g were purchased from Taconic Farms, Inc. Animals were housed 4 per cage, in controlled conditions of temperature (20-24° C.); humidity (60-70%) and 12 hrs light/dark cycle provided with food and water ad libitum. All experimental protocols were approved by the Institutional Animal Care and Use Committee of the VA hospital of Albany. Mice were allowed to acclimate to the conditions for 5 days prior to the start of treatments. Matrigel (BD Biosciences, San Jose Calif.) was thawed overnight at 4° C. and placed on ice. Aliquots of matrigel were placed into cold polypropylene tubes to prevent the matrigel from solidifying, and the angiogenesis promoter was added to the matrigel with or without an agonist. Matrigel plugs were subcutaneously injected as a triple injection in each animal at 100 µL/animal. At day 14 post plug implant, all animals were sacrificed in a CO$_2$ chamber, and matrigel plugs were collected. Plug hemoglobin content was analyzed from three implants per mouse (n=6 per group) to measure angiogenesis.

Hemoglobin determination of angiogenesis in matrigel plugs: the matrigel plugs dissected from the mouse were carefully stripped of any remaining peritoneum. The plugs were placed into a 0.5 mL tube of ddH$_2$O and homogenized for 5-10 min. The samples were spun at 4,000 rpm in a centrifuge for 10 min, and the supernatants were collected for hemoglobin measurement. 50 µL of supernatant were mixed with 50 µL Drabkin's reagent and allowed to sit at room temperature for 15-30 min, at which point 100 µL of this mixture were placed in a 96-well plate. Absorbance was measured with a Microplate Manager ELISA reader at 540 nm. Hemoglobin (Hb) concentration was determined by comparison with a standard curve in mg/mL. Hemoglobin concentration is a reflection of the number of blood vessels in the plugs.

In summary, newly designed dual Thyrointegrin antagonists were synthesized. Based on the structures of several potential anti-angiogenesis compounds, a new docking method was used to design novel dual Thyrointegrin antagonists that interact with integrin $\alpha v\beta_3$ and the thyroid receptors. Compounds were synthesized in a cost effective manner and exhibited strong inhibition of FGF-stimulated angiogenesis at low doses. The target of each compound was supported by modelling the fit of these compounds with the integrin $\alpha_v\beta_3$ receptors.

Dual thyrointegrin antagonists would have significant implications in various pathological angiogenesis-mediated disorders affecting an animal (e.g., a human being, a mammal, a non-human species of animal) such cancer, diabetic retinopathy, macular degeneration, inflammatory disorders, and atherothrombotic disorders. The dual thyrointegrin antagonists block both thyroid and integrin receptors and can also be used in disorders associated with hyperthyroidism. Accordingly, the present invention provides a method of treating an angiogenesis-mediated disorder and/or a disorder associated with hyperthyroidism of an animal by introducing the dual thyrointegrin antagonist of the present invention into the animal.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

APPENDIX A

TABLE OF EMBODIMENTS FOR CHEMICAL STRUCTURE 41

| $R_1$* | $R_2$* | $R_3$* | R** |
|---|---|---|---|
| I | —$(CH_2)_n NH_2$ | I | H |
| I | —$(CH_2)_n NH_2$ | H | H |
| H | —$(CH_2)_n NH_2$ | I | H |
| H | —$(CH_2)_n NH_2$ | OH | H |
| OH | —$(CH_2)_n NH_2$ | H | H |
| OH | —$(CH_2)_n NH_2$ | I | H |
| I | —$(CH_2)_n NH_2$ | OH | H |
| —$(CH_2)_n NH_2$ | H | I | H |
| —$(CH_2)_n NH_2$ | I | H | H |
| —$(CH_2)_n NH_2$ | I | I | H |
| —$(CH_2)_n NH_2$ | I | OH | H |
| —$(CH_2)_n NH_2$ | OH | I | H |
| —$(CH_2)_n NH_2$ | OH | H | H |
| —$(CH_2)_n NH_2$ | H | OH | H |
| I | H | —$(CH_2)_n NH_2$ | H |
| H | I | —$(CH_2)_n NH_2$ | H |
| I | I | —$(CH_2)_n NH_2$ | H |

APPENDIX A-continued

TABLE OF EMBODIMENTS FOR CHEMICAL STRUCTURE 41

| $R_1$* | $R_2$* | $R_3$* | R** |
|---|---|---|---|
| OH | I | —$(CH_2)_n NH_2$ | H |
| I | OH | —$(CH_2)_n NH_2$ | H |
| H | OH | —$(CH_2)_n NH_2$ | H |
| OH | H | —$(CH_2)_n NH_2$ | H |
| I | t-Boc$NCH_2CH_2CH_2O$—*** | I | H |
| I | HCl $NH_2CH_2CH_2CH_2O$— | I | methyl |
| I | HCl $NH_2CH_2CH_2CH_2O$— | I | H |
| I | (pyridine-HCl-CH2-NH(HCl)-CH2CH2CH2-O—) | I | methyl |
| I | (pyridine-HCl-CH2-NH(HCl)-CH2CH2CH2-O—) | I | H |
| I | (thiomorpholine-N-CH2CH2CH2-O—) | I | methyl |
| I | (thiomorpholine-N-CH2CH2CH2-O—) | I | H |
| I | (diethylamino-CH2CH2CH2-O—) | I | methyl |
| I | (diethylamino-CH2CH2CH2-O—) | I | H |
| I | (isopropyl-CH(CH3)-NH-CH2CH2CH2-O—) | I | methyl |
| I | (isopropyl-CH(CH3)-NH-CH2CH2CH2-O—) | I | H |

*n = 3, 4, or 5 in $(CH_2)_n$
**generally, R may be hydrogen, methyl, ethyl, propyl, isopropyl, etc for use as a prodrug
***T-Boc stands for tert-Butyloxycarbonyl

APPENDIX B

TABLE OF EMBODIMENTS FOR CHEMICAL STRUCTURE 42

| R** | $R_1$* | $R_2$* | $R_3$* | $R_4$*** |
|---|---|---|---|---|
| H | I | OH | I | I |
| H | I | —$(CH_2)_n NH_2$ | I | I |
| H | I |  | I | I |

APPENDIX B-continued

TABLE OF EMBODIMENTS FOR CHEMICAL STRUCTURE 42

| R** | $R_1$* | $R_2$* | $R_3$* | $R_4$*** |
|---|---|---|---|---|
| H | I | $H_2N-C(=O)-NH-CH_2CH_2-$ | I | I |
| H | I | $HO-NH-CH_2CH_2-$ | I | I |
| H | OH | I | I | I |
| H | $-(CH_2)_nNH_2$ | I | I | I |
| H | $HN=C(NH_2)-NH-CH_2CH_2-$ | I | I | I |
| H | $H_2N-C(=O)-NH-CH_2CH_2-$ | I | I | I |
| H | $HO-NH-CH_2CH_2-$ | I | I | I |
| H | I | I | OH | I |
| H | I | I | $-(CH_2)_nNH_2$ | I |
| H | I | I | $HN=C(NH_2)-NH-CH_2CH_2-$ | I |
| H | I | I | $H_2N-C(=O)-NH-CH_2CH_2-$ | I |
| H | I | I | $HO-NH-CH_2CH_2-$ | I |
| H | i-Pr | OH | i-Pr | Br |
| H | i-Pr | $-(CH_2)_nNH_2$ | i-Pr | Br |
| H | i-Pr | $HN=C(NH_2)-NH-CH_2CH_2-$ | i-Pr | Br |
| H | i-Pr | $H_2N-C(=O)-NH-CH_2CH_2-$ | i-Pr | Br |
| H | i-Pr | $HO-NH-CH_2CH_2-$ | i-Pr | Br |
| H | OH | i-Pr | i-Pr | Br |
| H | $-(CH_2)_nNH_2$ | i-Pr | i-Pr | Br |
| H | $HN=C(NH_2)-NH-CH_2CH_2-$ | i-Pr | i-Pr | Br |

APPENDIX B-continued

TABLE OF EMBODIMENTS FOR CHEMICAL STRUCTURE 42

| R** | R$_1$* | R$_2$* | R$_3$* | R$_4$*** |
|---|---|---|---|---|
| H | H$_2$N-C(O)-NH-CH$_2$CH$_2$— | i-Pr | i-Pr | Br |
| H | HO-NH-CH$_2$CH$_2$— | i-Pr | i-Pr | Br |
| H | | | | |
| H | i-Pr | i-Pr | OH | Br |
| H | i-Pr | i-Pr | —(CH$_2$)$_n$NH$_2$ | Br |
| H | i-Pr | i-Pr | HN=C(NH$_2$)-NH-CH$_2$CH$_2$— | Br |
| H | i-Pr | i-Pr | H$_2$N-C(O)-NH-CH$_2$CH$_2$— | Br |
| H | i-Pr | i-Pr | HO-NH-CH$_2$CH$_2$— | Br |
| H | 4-pyridyl-CH=CH-CH$_3$ | OH | i-Pr | Br |
| H | 4-pyridyl-CH=CH-CH$_3$ | —(CH$_2$)$_n$NH$_2$ | i-Pr | Br |
| H | 4-pyridyl-CH=CH-CH$_3$ | HN=C(NH$_2$)-NH-CH$_2$CH$_2$— | i-Pr | Br |
| H | 4-pyridyl-CH=CH-CH$_3$ | H$_2$N-C(O)-NH-CH$_2$CH$_2$— | i-Pr | Br |
| H | 4-pyridyl-CH=CH-CH$_3$ | HO-NH-CH$_2$CH$_2$— | i-Pr | Br |
| H | 4-pyridyl-CH=CH-CH$_3$ | i-Pr | OH | Br |
| H | 4-pyridyl-CH=CH-CH$_3$ | i-Pr | —(CH$_2$)$_n$NH$_2$ | Br |
| H | 4-pyridyl-CH=CH-CH$_3$ | i-Pr | HN=C(NH$_2$)-NH-CH$_2$CH$_2$— | Br |

APPENDIX B-continued

TABLE OF EMBODIMENTS FOR CHEMICAL STRUCTURE 42

| R** | R$_1$* | R$_2$* | R$_3$* | R$_4$*** |
|---|---|---|---|---|
| H | 4-(prop-1-en-1-yl)pyridine | i-Pr | NH$_2$C(O)NH-CH$_2$CH$_2$- | Br |
| H | 4-(prop-1-en-1-yl)pyridine | i-Pr | HO-NH-CH$_2$CH$_2$- | Br |
| H | OH | 4-(prop-1-en-1-yl)pyridine | i-Pr | Br |
| H | —(CH$_2$)$_n$NH$_2$ | 4-(prop-1-en-1-yl)pyridine | i-Pr | Br |
| H | HN=C(NH$_2$)NH-CH$_2$CH$_2$- | 4-(prop-1-en-1-yl)pyridine | i-Pr | Br |
| H | NH$_2$C(O)NH-CH$_2$CH$_2$- | 4-(prop-1-en-1-yl)pyridine | i-Pr | Br |
| H | HO-NH-CH$_2$CH$_2$- | 4-(prop-1-en-1-yl)pyridine | i-Pr | Br |
| H | OH | i-Pr | 4-(prop-1-en-1-yl)pyridine | Br |
| H | —(CH$_2$)$_n$NH$_2$ | i-Pr | 4-(prop-1-en-1-yl)pyridine | Br |
| H | HN=C(NH$_2$)NH-CH$_2$CH$_2$- | i-Pr | 4-(prop-1-en-1-yl)pyridine | Br |
| H | NH$_2$C(O)NH-CH$_2$CH$_2$- | i-Pr | 4-(prop-1-en-1-yl)pyridine | Br |
| H | HO-NH-CH$_2$CH$_2$- | i-Pr | 4-(prop-1-en-1-yl)pyridine | Br |
| H | i-Pr | OH | 4-(prop-1-en-1-yl)pyridine | Br |

APPENDIX B-continued
TABLE OF EMBODIMENTS FOR CHEMICAL STRUCTURE 42
| R** | R₁* | R₂* | R₃* | R₄*** |
|---|---|---|---|---|
| H | i-Pr | —(CH₂)ₙNH₂ | 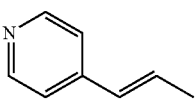 | Br |
| H | i-Pr | 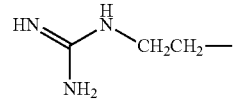 | 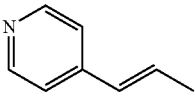 | Br |
| H | i-Pr | 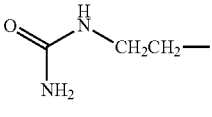 | 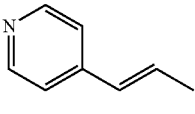 | Br |
| H | i-Pr | 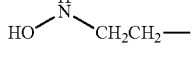 | 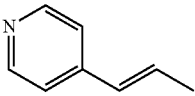 | Br |
| H | i-Pr | 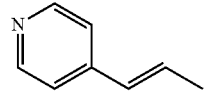 | OH | Br |
| H | i-Pr | 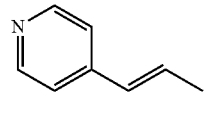 | —(CH₂)ₙNH₂ | Br |
| H | i-Pr | 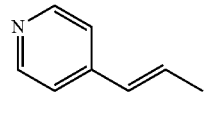 | 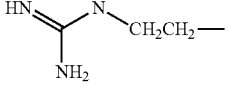 | Br |
| H | i-Pr | 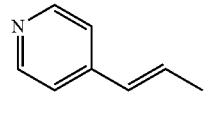 | 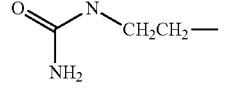 | Br |
| H | i-Pr | 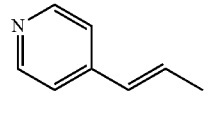 | 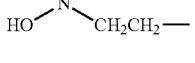 | Br |
| H | 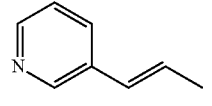 | OH | i-Pr | Br |
| H | 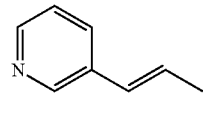 | —(CH₂)ₙNH₂ | i-Pr | Br |
| H | 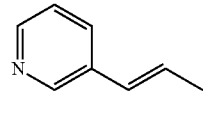 | 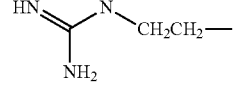 | i-Pr | Br |
| H | 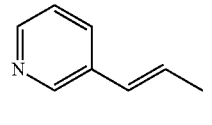 | 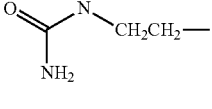 | i-Pr | Br |

APPENDIX B-continued

TABLE OF EMBODIMENTS FOR CHEMICAL STRUCTURE 42

| R** | $R_1$* | $R_2$* | $R_3$* | $R_4$*** |
|---|---|---|---|---|
| H | 3-pyridyl-CH=CH-CH₂- | HO-NH-CH₂CH₂- | i-Pr | Br |
| H | 3-pyridyl-CH=CH-CH₂- | | | |
| H | 3-pyridyl-CH=CH-CH₂- | i-Pr | OH | Br |
| H | 3-pyridyl-CH=CH-CH₂- | i-Pr | —(CH₂)ₙNH₂ | Br |
| H | 3-pyridyl-CH=CH-CH₂- | i-Pr | HN=C(NH₂)-NH-CH₂CH₂- | Br |
| H | 3-pyridyl-CH=CH-CH₂- | i-Pr | H₂N-C(O)-NH-CH₂CH₂- | Br |
| H | 3-pyridyl-CH=CH-CH₂- | i-Pr | HO-NH-CH₂CH₂- | Br |
| H | OH | 3-pyridyl-CH=CH-CH₂- | i-Pr | Br |
| H | —(CH₂)ₙNH₂ | 3-pyridyl-CH=CH-CH₂- | i-Pr | Br |
| H | HN=C(NH₂)-NH-CH₂CH₂- | 3-pyridyl-CH=CH-CH₂- | i-Pr | Br |
| H | H₂N-C(O)-NH-CH₂CH₂- | 3-pyridyl-CH=CH-CH₂- | i-Pr | Br |
| H | HO-NH-CH₂CH₂- | 3-pyridyl-CH=CH-CH₂- | i-Pr | Br |
| H | OH | i-Pr | 3-pyridyl-CH=CH-CH₂- | Br |

APPENDIX B-continued
TABLE OF EMBODIMENTS FOR CHEMICAL STRUCTURE 42
| R** | R₁* | R₂* | R₃* | R₄*** |
|---|---|---|---|---|
| H | —(CH₂)ₙNH₂ | i-Pr | 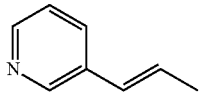 | Br |
| H | 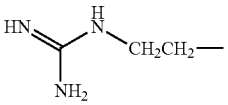 | i-Pr | 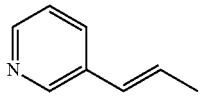 | Br |
| H | 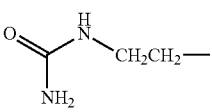 | i-Pr | 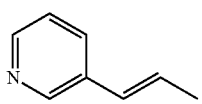 | Br |
| H | 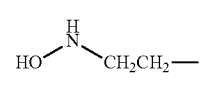 | i-Pr | 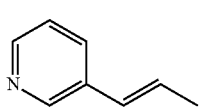 | Br |
| H | i-Pr | OH | 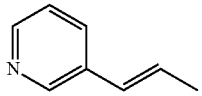 | Br |
| H | i-Pr | —(CH₂)ₙNH₂ | 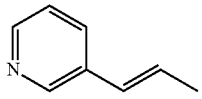 | Br |
| H | i-Pr | 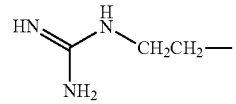 | 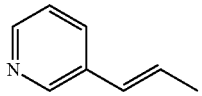 | Br |
| H | i-Pr | 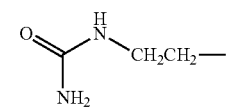 | 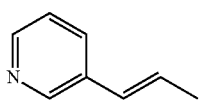 | Br |
| H | i-Pr | 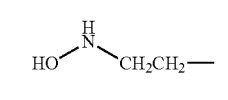 | 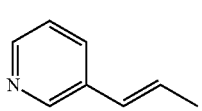 | Br |
| H | i-Pr | 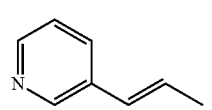 | OH | Br |
| H | i-Pr | 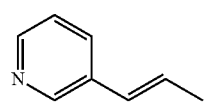 | —(CH₂)ₙNH₂ | Br |
| H | i-Pr | 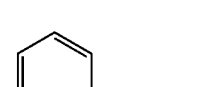 | 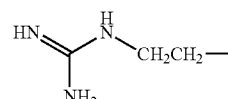 | Br |
| H | i-Pr | 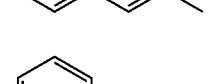 | 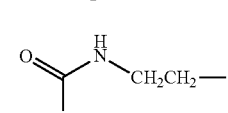 | Br |

APPENDIX B-continued

TABLE OF EMBODIMENTS FOR CHEMICAL STRUCTURE 42

| R** | R₁* | R₂* | R₃* | R₄*** |
|---|---|---|---|---|
| H | i-Pr | 3-(1-propenyl)pyridine | HO-NH-CH₂CH₂- | Br |
| H | 2-(1-propenyl)pyridine | OH | i-Pr | Br |
| H | 2-(1-propenyl)pyridine | —(CH₂)ₙNH₂ | i-Pr | Br |
| H | 2-(1-propenyl)pyridine | HN=C(NH₂)-NH-CH₂CH₂- | i-Pr | Br |
| H | 2-(1-propenyl)pyridine | O=C(NH₂)-NH-CH₂CH₂- | i-Pr | Br |
| H | 2-(1-propenyl)pyridine | HO-NH-CH₂CH₂- | i-Pr | Br |
| H | 2-(1-propenyl)pyridine | | | |
| H | 2-(1-propenyl)pyridine | i-Pr | OH | Br |
| H | 2-(1-propenyl)pyridine | i-Pr | —(CH₂)ₙNH₂ | Br |
| H | 2-(1-propenyl)pyridine | i-Pr | HN=C(NH₂)-NH-CH₂CH₂- | Br |
| H | 2-(1-propenyl)pyridine | i-Pr | O=C(NH₂)-NH-CH₂CH₂- | Br |
| H | 2-(1-propenyl)pyridine | i-Pr | HO-NH-CH₂CH₂- | Br |
| H | OH | 2-(1-propenyl)pyridine | i-Pr | Br |

APPENDIX B-continued
TABLE OF EMBODIMENTS FOR CHEMICAL STRUCTURE 42
| R** | R₁* | R₂* | R₃* | R₄*** |
|---|---|---|---|---|
| H | —(CH₂)ₙNH₂ | 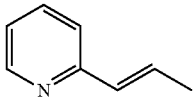 | i-Pr | Br |
| H | 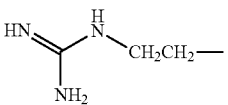 | 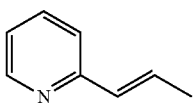 | i-Pr | Br |
| H | 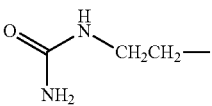 | 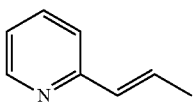 | i-Pr | Br |
| H | 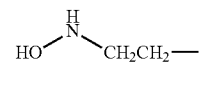 | 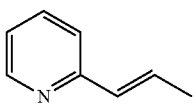 | i-Pr | Br |
| H | OH | i-Pr | 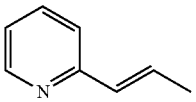 | Br |
| H | —(CH₂)ₙNH₂ | i-Pr | 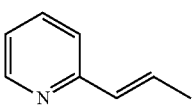 | Br |
| H | 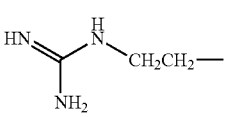 | i-Pr | 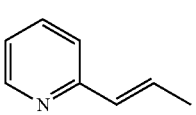 | Br |
| H | 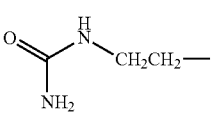 | i-Pr | 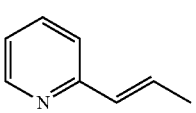 | Br |
| H | 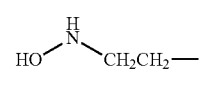 | i-Pr | 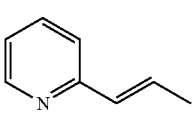 | Br |
| H | i-Pr | OH | 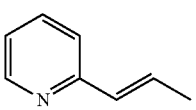 | Br |
| H | i-Pr | —(CH₂)ₙNH₂ | 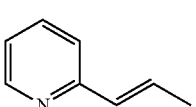 | Br |
| H | i-Pr | 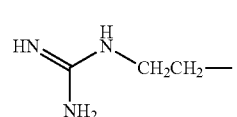 | 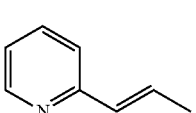 | Br |
| H | i-Pr | 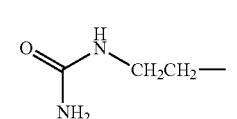 | 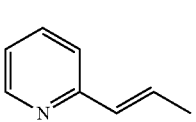 | Br |

APPENDIX B-continued

TABLE OF EMBODIMENTS FOR CHEMICAL STRUCTURE 42

| R** | R₁* | R₂* | R₃* | R₄*** |
|---|---|---|---|---|
| H | i-Pr | 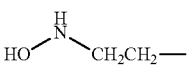 HO-NH-CH₂CH₂— | 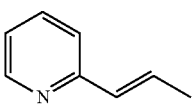 2-pyridyl-CH=CH-CH₃ | Br |
| H | i-Pr | 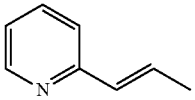 2-pyridyl-CH=CH-CH₃ | OH | Br |
| H | i-Pr | 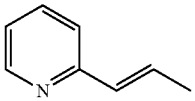 2-pyridyl-CH=CH-CH₃ | —(CH₂)ₙNH₂ | Br |
| H | i-Pr | 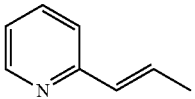 2-pyridyl-CH=CH-CH₃ | 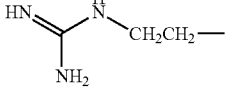 HN=C(NH₂)-NH-CH₂CH₂— | Br |
| H | i-Pr | 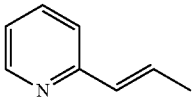 2-pyridyl-CH=CH-CH₃ | 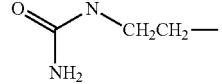 H₂N-C(=O)-NH-CH₂CH₂— | Br |
| H | i-Pr | 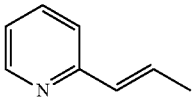 2-pyridyl-CH=CH-CH₃ | 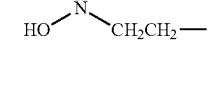 HO-NH-CH₂CH₂— | Br |
| H | 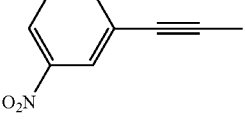 3-O₂N-C₆H₄-C≡C- | OH | i-Pr | Me |
| H | 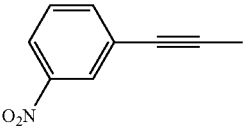 3-O₂N-C₆H₄-C≡C- | —(CH₂)ₙNH₂ | i-Pr | Me |
| H | 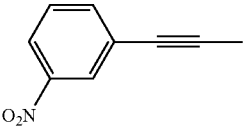 3-O₂N-C₆H₄-C≡C- | 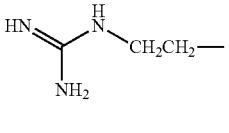 HN=C(NH₂)-NH-CH₂CH₂— | i-Pr | Me |
| H | 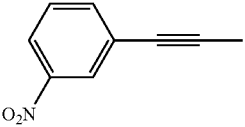 3-O₂N-C₆H₄-C≡C- | 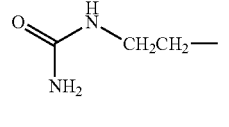 H₂N-C(=O)-NH-CH₂CH₂— | i-Pr | Me |
| H | 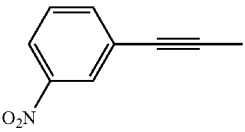 3-O₂N-C₆H₄-C≡C- | 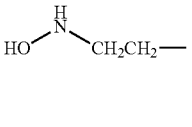 HO-NH-CH₂CH₂— | i-Pr | Me |
| H | OH | 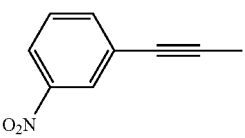 3-O₂N-C₆H₄-C≡C- | i-Pr | Me |

APPENDIX B-continued
TABLE OF EMBODIMENTS FOR CHEMICAL STRUCTURE 42
| R** | R₁* | R₂* | R₃* | R₄*** |
|---|---|---|---|---|
| H | —(CH₂)ₙNH₂ | 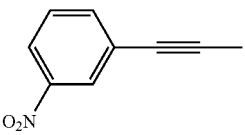 | i-Pr | Me |
| H | 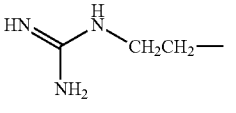 | 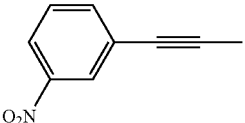 | i-Pr | Me |
| H | 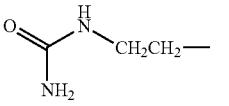 | 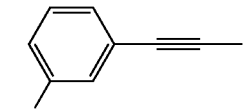 | i-Pr | Me |
| H | 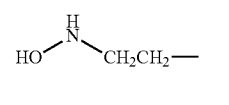 | 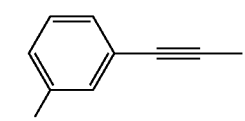 | i-Pr | Me |
| H | 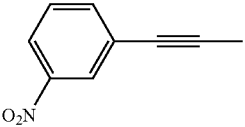 | i-Pr | OH | Me |
| H | 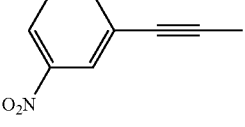 | i-Pr | —(CH₂)ₙNH₂ | Me |
| H | 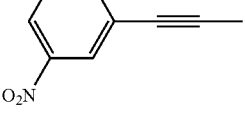 | i-Pr | 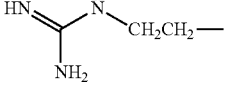 | Me |
| H | 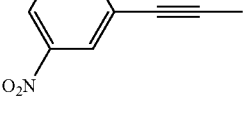 | i-Pr | 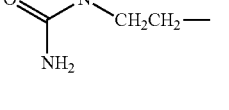 | Me |
| H | 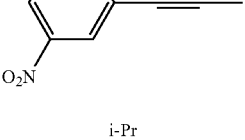 | i-Pr | 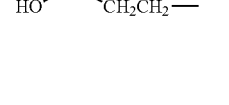 | Me |
| H | i-Pr | 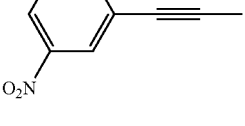 | OH | Me |

APPENDIX B-continued

TABLE OF EMBODIMENTS FOR CHEMICAL STRUCTURE 42

| R** | R$_1$* | R$_2$* | R$_3$* | R$_4$*** |
|---|---|---|---|---|
| H | i-Pr | 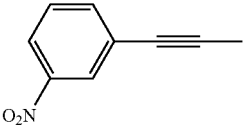 3-nitrophenylethynyl | —(CH$_2$)$_n$NH$_2$ | Me |
| H | i-Pr | 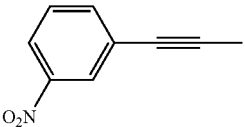 3-nitrophenylethynyl | 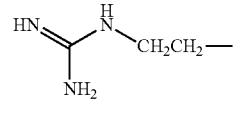 guanidinoethyl | Me |
| H | i-Pr | 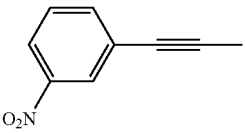 3-nitrophenylethynyl | 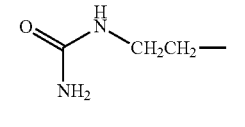 ureidoethyl | Me |
| H | i-Pr | 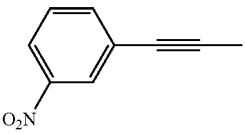 3-nitrophenylethynyl | 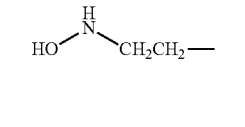 HO-NH-CH$_2$CH$_2$— | Me |
| H | i-Pr | OH | 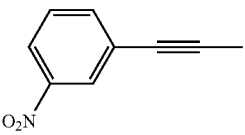 3-nitrophenylethynyl | Me |
| H | i-Pr | —(CH$_2$)$_n$NH$_2$ | 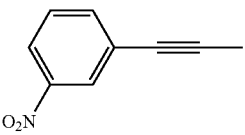 3-nitrophenylethynyl | Me |
| H | i-Pr | 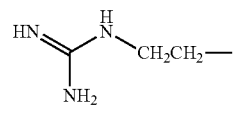 guanidinoethyl | 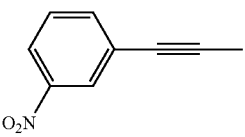 3-nitrophenylethynyl | Me |
| H | i-Pr | 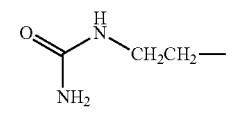 ureidoethyl | 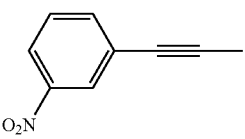 3-nitrophenylethynyl | Me |
| H | i-Pr | 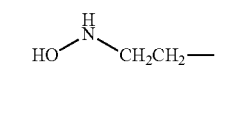 HO-NH-CH$_2$CH$_2$— | 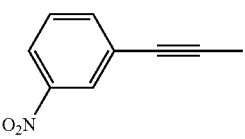 3-nitrophenylethynyl | Me |
| H | OH | i-Pr | 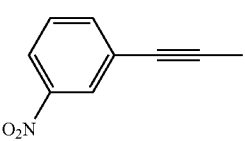 3-nitrophenylethynyl | Me |

APPENDIX B-continued
TABLE OF EMBODIMENTS FOR CHEMICAL STRUCTURE 42
| R** | R₁* | R₂* | R₃* | R₄*** |
|---|---|---|---|---|
| H | —(CH₂)ₙNH₂ | i-Pr | 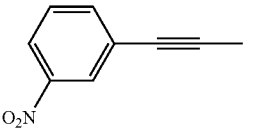 | Me |
| H | 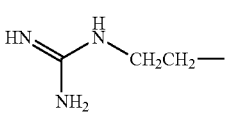 | i-Pr | 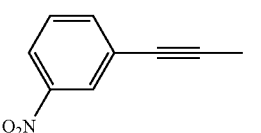 | Me |
| H | 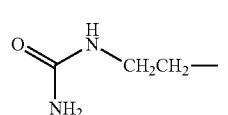 | i-Pr | 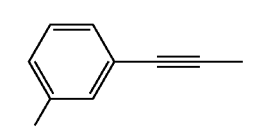 | Me |
| H | 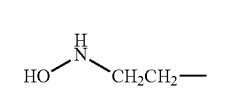 | i-Pr | 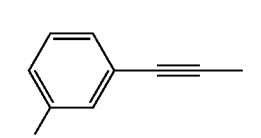 | Me |
| H | 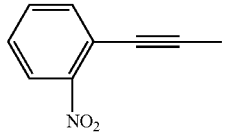 | OH | i-Pr | Me |
| H | 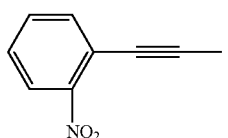 | —(CH₂)ₙNH₂ | i-Pr | Me |
| H | 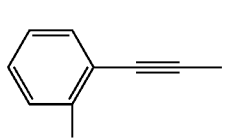 | 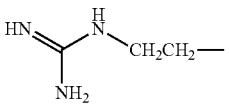 | i-Pr | Me |
| H | 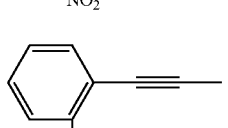 | 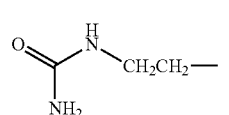 | i-Pr | Me |
| H | 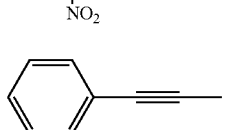 | 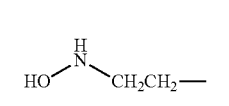 | i-Pr | Me |
| H | OH | 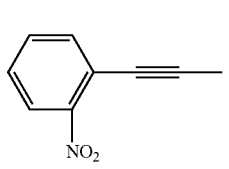 | i-Pr | Me |

APPENDIX B-continued
TABLE OF EMBODIMENTS FOR CHEMICAL STRUCTURE 42
| R** | R$_1$* | R$_2$* | R$_3$* | R$_4$*** |
|---|---|---|---|---|
| H | —(CH$_2$)$_n$NH$_2$ | 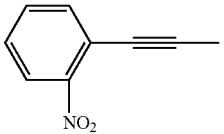 | i-Pr | Me |
| H | 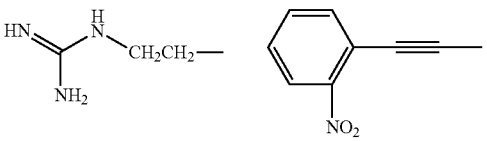 | 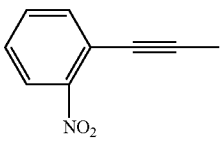 | i-Pr | Me |
| H | 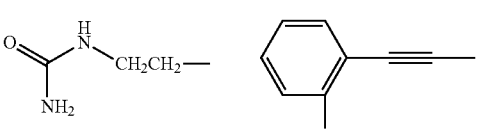 | 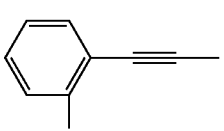 | i-Pr | Me |
| H | 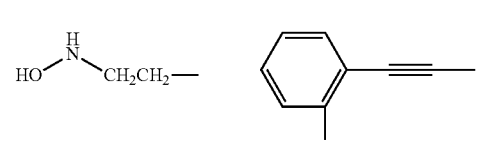 | 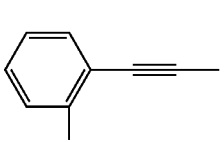 | i-Pr | Me |
| H |  | i-Pr | OH | Me |
| H | 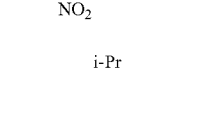 | i-Pr | —(CH$_2$)$_n$NH$_2$ | Me |
| H |  | i-Pr | 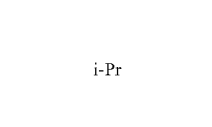 | Me |
| H |  | i-Pr | 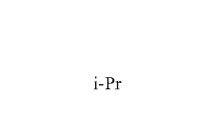 | Me |
| H |  | i-Pr | 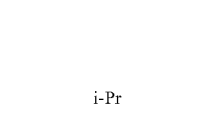 | Me |
| H | i-Pr |  | OH | Me |

APPENDIX B-continued
TABLE OF EMBODIMENTS FOR CHEMICAL STRUCTURE 42
| R** | R₁* | R₂* | R₃* | R₄*** |
|---|---|---|---|---|
| H | i-Pr | 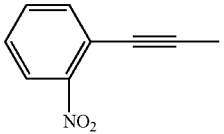 | —(CH₂)ₙNH₂ | Me |
| H | i-Pr | 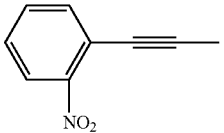 | 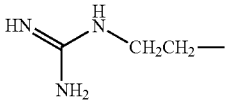 | Me |
| H | i-Pr | 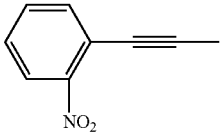 | 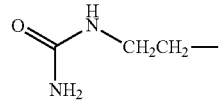 | Me |
| H | i-Pr | 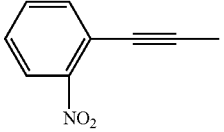 | 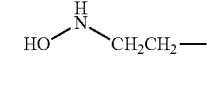 | Me |
| H | i-Pr | OH | 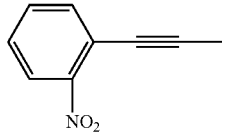 | Me |
| H | i-Pr | —(CH₂)ₙNH₂ | 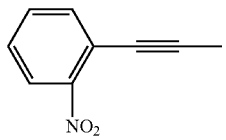 | Me |
| H | i-Pr | 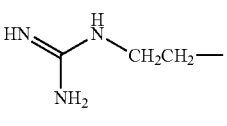 | 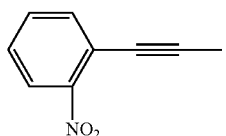 | Me |
| H | i-Pr | 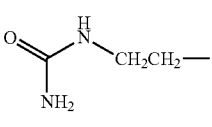 | 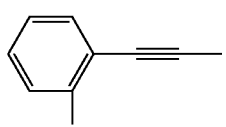 | Me |
| H | i-Pr | 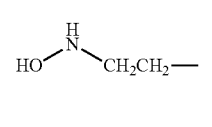 | 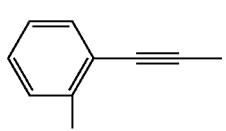 | Me |
| H | OH | i-Pr | 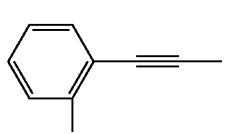 | Me |

APPENDIX B-continued
TABLE OF EMBODIMENTS FOR CHEMICAL STRUCTURE 42
| R** | R₁* | R₂* | R₃* | R₄*** |
|---|---|---|---|---|
| H | —(CH₂)ₙNH₂ | i-Pr | 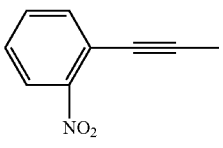 | Me |
| H | 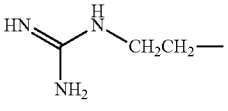 | i-Pr | 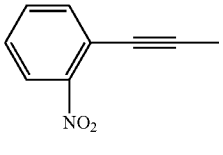 | Me |
| H | 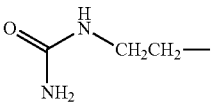 | i-Pr | 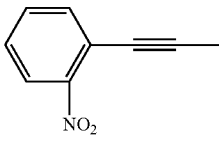 | Me |
| H | 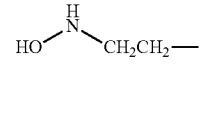 | i-Pr | 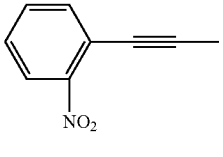 | Me |
| H | i-Pr | OH | H | t-Bu |
| H | i-Pr | —(CH₂)ₙNH₂ | H | t-Bu |
| H | i-Pr | 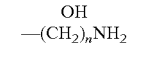 | H | t-Bu |
| H | i-Pr | 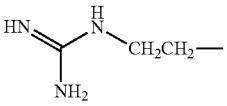 | H | t-Bu |
| H | i-Pr | 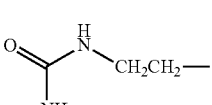 | H | t-Bu |
| H | i-Pr | H | OH | t-Bu |
| H | i-Pr | H | —(CH₂)ₙNH₂ | t-Bu |
| H | i-Pr | H | 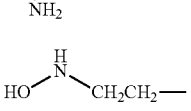 | t-Bu |
| H | i-Pr | H | 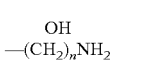 | t-Bu |
| H | i-Pr | H | 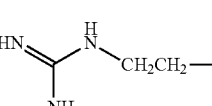 | t-Bu |
| H | H | i-Pr | OH | t-Bu |
| H | H | i-Pr | —(CH₂)ₙNH₂ | t-Bu |
| H | H | i-Pr | 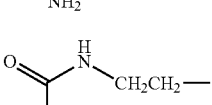 | t-Bu |

APPENDIX B-continued

TABLE OF EMBODIMENTS FOR CHEMICAL STRUCTURE 42

| R** | $R_1$* | $R_2$* | $R_3$* | $R_4$*** |
|---|---|---|---|---|
| H | H | i-Pr | H₂N-C(=O)-NH-CH₂CH₂— | t-Bu |
| H | H | i-Pr | HO-NH-CH₂CH₂— | t-Bu |
| H | H | OH | i-Pr | t-Bu |
| H | H | —(CH₂)ₙNH₂ | i-Pr | t-Bu |
| H | H | HN=C(NH₂)-NH-CH₂CH₂— | i-Pr | t-Bu |
| H | H | H₂N-C(=O)-NH-CH₂CH₂— | i-Pr | t-Bu |
| H | H | HO-NH-CH₂CH₂— | i-Pr | t-Bu |
| H | OH | H | i-Pr | t-Bu |
| H | —(CH₂)ₙNH₂ | H | i-Pr | t-Bu |
| H | HN=C(NH₂)-NH-CH₂CH₂— | H | i-Pr | t-Bu |
| H | H₂N-C(=O)-NH-CH₂CH₂— | H | i-Pr | t-Bu |
| H | HO-NH-CH₂CH₂— | H | i-Pr | t-Bu |
| H | OH | i-Pr | H | t-Bu |
| H | —(CH₂)ₙNH₂ | i-Pr | H | t-Bu |
| H | HN=C(NH₂)-NH-CH₂CH₂— | i-Pr | H | t-Bu |
| H | H₂N-C(=O)-NH-CH₂CH₂— | i-Pr | H | t-Bu |
| H | HO-NH-CH₂CH₂— | i-Pr | H | t-Bu |

*n = 3, 4, or 5 in (CH₂)ₙ; i-Pr stands for isopropyl
**Generally, R may be hydrogen, methyl, ethyl, propyl, isopropyl, etc for use as a prodrug
***Me stands for methyl; t-Bu stands for tert-Butyl

What is claimed is:

1. A dual thyrointegrin antagonist having the chemical structure of

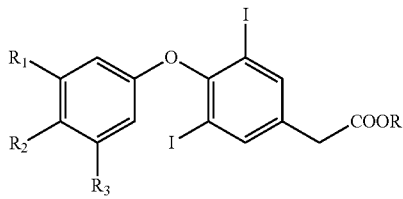

wherein R is selected from the group consisting of hydrogen, methyl, ethyl, propyl, and isopropyl;
wherein X is —$(CH_2)_nNH_2$ such that n is 3, 4, or 5;
wherein $R_1$ is I, $R_2$ is X, and $R_3$ is I.

2. A method for treating an angiogenesis-mediated disorder and/or a hyperthyroidism disorder of an animal, said method comprising:
introducing the dual thyrointegrin antagonist of claim 1 into the animal for treating the angiogenesis-mediated disorder and/or the hyperthyroidism disorder.

3. The method of claim 2, wherein said treating comprises treating the angiogenesis-mediated disorder, and wherein the angiogenesis-mediated disorder is selected from the group consisting of cancer, diabetic retinopathy, macular degeneration, an inflammatory disorder, and an atherothrombotic disorder.

4. The method of claim 2, wherein said treating comprises treating the hyperthyroidism disorder.

5. The method of claim 2, wherein the animal is a human being.

* * * * *